(12) United States Patent
Taylor et al.

(10) Patent No.: US 9,918,729 B2
(45) Date of Patent: Mar. 20, 2018

(54) SNARING SYSTEMS AND METHODS

(71) Applicant: The Spectranetics Corporation, Colorado Springs, CO (US)

(72) Inventors: Kevin D. Taylor, Colorado Springs, CO (US); George Burton, Colorado Springs, CO (US); Dave Atwell, Colorado Springs, CO (US); Wade Bowe, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 141 days.

(21) Appl. No.: 14/978,731

(22) Filed: Dec. 22, 2015

(65) Prior Publication Data
US 2016/0183954 A1    Jun. 30, 2016

Related U.S. Application Data

(63) Continuation of application No. 12/878,648, filed on Sep. 9, 2010, now Pat. No. 9,220,523.

(60) Provisional application No. 61/242,225, filed on Sep. 14, 2009.

(51) Int. Cl.
*A61B 17/221* (2006.01)
*A61B 17/34* (2006.01)
*A61N 1/05* (2006.01)

(52) U.S. Cl.
CPC ........ *A61B 17/221* (2013.01); *A61B 17/3468* (2013.01); *A61B 2017/2217* (2013.01); *A61N 2001/0578* (2013.01)

(58) Field of Classification Search
CPC .............. A61B 17/221; A61B 17/3468; A61B 2017/2217; A61B 17/32056; A61B 2017/2212; A61B 2017/2215; A61B 2017/22035
See application file for complete search history.

(56) References Cited

U.S. PATENT DOCUMENTS

| | | | |
|---|---|---|---|
| 1,891,497 | A | 12/1932 | Birkenmaier |
| 2,446,710 | A | 8/1948 | Makaroff |
| 2,615,402 | A | 10/1952 | Chamberlain, Jr. |
| 2,627,137 | A | 2/1953 | Koski |
| 2,856,933 | A | 10/1958 | Scharf et al. |

(Continued)

FOREIGN PATENT DOCUMENTS

| | | |
|---|---|---|
| DE | 19964093 B4 | 11/2001 |
| EP | 169784 A2 | 1/1986 |

(Continued)

OTHER PUBLICATIONS

Smith et al. Extraction of Transvenous Pacing and ICD Leads; PACE vol. 31 Jun. 2008 pp. 736-752.

*Primary Examiner* — Katrina Stransky
(74) *Attorney, Agent, or Firm* — Faegre Baker Daniels LLP

(57) ABSTRACT

Snaring systems and methods involve engaging objects such as pacemaker pacing leads within a patient. Physicians can use snaring systems having loops, tags, and roller mechanisms to remove a pacing leads from a patient. For example, snaring systems can be inserted through a jugular access site, engaged with a pacemaker pacing lead, and withdrawn through the jugular access site so as to remove a portion of the pacing lead. Lead extraction techniques can be employed to further dislodge the pacing lead from the patient.

20 Claims, 21 Drawing Sheets

(56) References Cited

U.S. PATENT DOCUMENTS

| | | |
|---|---|---|
| 3,068,608 A | 12/1962 | Counts |
| 3,220,138 A | 11/1965 | Greenfield |
| 3,955,578 A | 5/1976 | Chamness et al. |
| 4,208,827 A | 6/1980 | Starkey |
| 4,250,653 A | 2/1981 | Davies |
| 4,471,777 A | 9/1984 | McCorkle, Jr. |
| 4,506,471 A | 3/1985 | Riead |
| 4,506,472 A | 3/1985 | Barman |
| 4,582,056 A | 4/1986 | McCorkle et al. |
| 4,636,346 A | 1/1987 | Gold et al. |
| 4,824,435 A | 4/1989 | Giesy et al. |
| 4,943,289 A | 7/1990 | Goode et al. |
| 4,988,347 A | 1/1991 | Goode et al. |
| 5,011,482 A | 4/1991 | Goode et al. |
| 5,013,310 A | 5/1991 | Goode et al. |
| 5,036,854 A | 8/1991 | Schollmeyer et al. |
| 5,098,440 A | 3/1992 | Hillstead |
| 5,163,938 A | 11/1992 | Kambara et al. |
| 5,171,233 A | 12/1992 | Amplatz et al. |
| 5,171,314 A | 12/1992 | Dulebohn |
| 5,192,286 A | 3/1993 | Phan et al. |
| 5,207,683 A | 5/1993 | Goode et al. |
| 5,224,935 A | 7/1993 | Hollands |
| 5,247,942 A | 9/1993 | Prather et al. |
| 5,263,493 A | 11/1993 | Avitall |
| 5,282,478 A | 2/1994 | Fleischhaker et al. |
| 5,312,423 A | 5/1994 | Rosenbluth et al. |
| 5,342,371 A | 8/1994 | Welter et al. |
| 5,387,219 A | 2/1995 | Rappe |
| 5,417,684 A | 5/1995 | Jackson et al. |
| 5,443,472 A | 8/1995 | Li |
| 5,509,902 A | 4/1996 | Raulerson |
| 5,522,819 A | 6/1996 | Graves et al. |
| 5,555,883 A | 9/1996 | Avitall |
| 5,562,678 A | 10/1996 | Booker |
| 5,611,803 A | 3/1997 | Heaven et al. |
| 5,613,973 A | 3/1997 | Jackson et al. |
| 5,632,749 A | 5/1997 | Goode et al. |
| 5,637,098 A | 6/1997 | Bierman |
| 5,653,716 A | 8/1997 | Malo et al. |
| 5,681,347 A | 10/1997 | Cathcart et al. |
| 5,693,059 A | 12/1997 | Yoon |
| 5,697,936 A | 12/1997 | Shipko et al. |
| 5,769,858 A | 6/1998 | Pearson et al. |
| 5,782,839 A | 7/1998 | Hart et al. |
| 5,823,971 A | 10/1998 | Robinson et al. |
| 5,836,947 A | 11/1998 | Fleischman et al. |
| 5,868,754 A | 2/1999 | Levine et al. |
| 6,088,609 A | 7/2000 | Larison, II |
| 6,090,129 A | 7/2000 | Ouchi |
| 6,093,195 A | 7/2000 | Ouchi |
| 6,136,005 A | 10/2000 | Goode et al. |
| 6,167,315 A | 12/2000 | Coe et al. |
| 6,290,693 B1 | 9/2001 | Jung et al. |
| 6,375,639 B1 | 4/2002 | Duplessie et al. |
| 6,379,319 B1 | 4/2002 | Garibotto et al. |
| 6,432,115 B1 | 8/2002 | Mollenauer et al. |
| 6,478,777 B1 | 11/2002 | Honeck et al. |
| 6,500,182 B2 | 12/2002 | Foster |
| 6,511,492 B1 | 1/2003 | Rosenbluth et al. |
| 6,517,550 B1 | 2/2003 | Andras Konya et al. |
| 6,544,269 B2 | 4/2003 | Osborne et al. |
| 6,575,988 B2 | 6/2003 | Rousseau |
| 6,598,335 B2 | 7/2003 | Akhtar et al. |
| 6,687,548 B2 | 2/2004 | Goode |
| 6,695,813 B1 | 2/2004 | Boyle et al. |
| 6,712,826 B2 | 3/2004 | Lui |
| 6,743,228 B2 | 6/2004 | Lee et al. |
| 6,840,000 B2 | 1/2005 | Akhtar et al. |
| 6,893,450 B2 | 5/2005 | Foster |
| 7,041,108 B2 | 5/2006 | Lippitt et al. |
| 7,101,378 B2 | 9/2006 | Salameh et al. |
| 7,210,210 B2 | 5/2007 | Lippitt et al. |
| 7,359,756 B2 | 4/2008 | Goode |
| 7,470,256 B2 | 12/2008 | Lampropoulos et al. |
| 7,499,756 B2 | 3/2009 | Bowe et al. |
| 7,520,881 B2 | 4/2009 | Foushee et al. |
| 7,524,281 B2 | 4/2009 | Chu et al. |
| 7,641,646 B2 | 1/2010 | Kennedy, II |
| 7,651,503 B1 | 1/2010 | Coe et al. |
| 7,651,504 B2 | 1/2010 | Goode et al. |
| 7,713,275 B2 | 5/2010 | Greenberg et al. |
| 7,727,253 B2 | 6/2010 | Ackerman et al. |
| 7,731,693 B2 | 6/2010 | Melsheimer |
| 7,753,917 B2 | 7/2010 | Urbanski et al. |
| 7,753,918 B2 | 7/2010 | Hartley et al. |
| 7,758,592 B2 | 7/2010 | Ayala et al. |
| 7,776,052 B2 | 8/2010 | Greenberg et al. |
| 7,824,342 B2 | 11/2010 | Minosawa et al. |
| 7,871,414 B2 | 1/2011 | Hardin et al. |
| 7,993,359 B1 | 8/2011 | Atwell et al. |
| 8,070,693 B2 | 12/2011 | Ayala et al. |
| 8,109,986 B2 | 2/2012 | Styrc |
| 8,128,636 B2 | 3/2012 | Lui et al. |
| 8,137,291 B2 | 3/2012 | Melsheimer |
| 8,192,430 B2 | 6/2012 | Goode et al. |
| 8,252,019 B2 | 8/2012 | Fleming et al. |
| 8,323,179 B2 | 12/2012 | Chu et al. |
| 8,326,437 B2 | 12/2012 | Cully et al. |
| 8,469,970 B2 | 6/2013 | Diamant et al. |
| 8,551,139 B2 | 10/2013 | Surti et al. |
| 8,597,303 B2 | 12/2013 | Hammack et al. |
| 8,702,625 B2 | 4/2014 | Ayala et al. |
| 8,715,205 B2 | 5/2014 | Carter et al. |
| 8,740,969 B2 | 6/2014 | Jensen et al. |
| 8,747,295 B2 | 6/2014 | Chu et al. |
| 8,758,326 B2 | 6/2014 | Hennessy |
| 8,814,900 B2 | 8/2014 | Fleming et al. |
| 9,220,523 B2 | 12/2015 | Taylor et al. |
| 2002/0007204 A1 | 1/2002 | Goode |
| 2002/0010475 A1 | 1/2002 | Lui |
| 2002/0087100 A1 | 7/2002 | Onuki et al. |
| 2002/0107526 A1 | 8/2002 | Greenberg et al. |
| 2002/0123765 A1 | 9/2002 | Sepetka et al. |
| 2003/0187457 A1 | 10/2003 | Weber |
| 2004/0116939 A1 | 6/2004 | Goode |
| 2004/0123765 A1 | 7/2004 | Furusawa et al. |
| 2004/0153096 A1 | 8/2004 | Goode et al. |
| 2004/0199200 A1* | 10/2004 | Teague ............... A61B 17/221 606/200 |
| 2004/0220604 A1 | 11/2004 | Fogarty et al. |
| 2004/0243168 A1 | 12/2004 | Ferrera et al. |
| 2005/0043743 A1 | 2/2005 | Dennis |
| 2005/0096650 A1 | 5/2005 | Ouchi |
| 2005/0177022 A1 | 8/2005 | Chu et al. |
| 2005/0209609 A1 | 9/2005 | Wallace |
| 2006/0073904 A1 | 4/2006 | Novak |
| 2006/0100545 A1 | 5/2006 | Ayala et al. |
| 2006/0149295 A1 | 7/2006 | Fleming, III |
| 2007/0123804 A1 | 5/2007 | Ayala et al. |
| 2007/0191919 A1 | 8/2007 | Lui et al. |
| 2008/0147061 A1 | 6/2008 | Goode et al. |
| 2008/0147111 A1 | 6/2008 | Johnson et al. |
| 2008/0208075 A1 | 8/2008 | Goldenberg |
| 2008/0221587 A1 | 9/2008 | Schwartz |
| 2009/0112244 A1 | 4/2009 | Freudenthal |
| 2009/0234367 A1 | 9/2009 | Verma |
| 2010/0042107 A1 | 2/2010 | Merrifield |
| 2010/0252049 A1 | 10/2010 | Kost |
| 2011/0098720 A1 | 4/2011 | Taylor et al. |
| 2011/0106099 A1 | 5/2011 | Duffy et al. |
| 2011/0106107 A1 | 5/2011 | Binmoeller et al. |
| 2011/0112548 A1 | 5/2011 | Fifer et al. |
| 2011/0238078 A1 | 9/2011 | Goode et al. |
| 2012/0165827 A1 | 6/2012 | Khairkhahan et al. |
| 2012/0165850 A1 | 6/2012 | Deckard et al. |
| 2012/0310214 A1 | 12/2012 | Hennessy |
| 2013/0006261 A1 | 1/2013 | Lampropoulos et al. |
| 2013/0006262 A1 | 1/2013 | Lampropoulos et al. |
| 2013/0131688 A1 | 5/2013 | Schwartz |
| 2013/0172714 A1 | 7/2013 | Li et al. |
| 2013/0184738 A1 | 7/2013 | Laroya et al. |
| 2013/0184741 A1 | 7/2013 | Laroya et al. |
| 2013/0197476 A1 | 8/2013 | Karpiel |

(56) References Cited

U.S. PATENT DOCUMENTS

| | | |
|---|---|---|
| 2013/0238024 A1 | 9/2013 | Taylor et al. |
| 2013/0261638 A1 | 10/2013 | Diamant et al. |
| 2014/0155930 A1 | 6/2014 | Bennett et al. |
| 2014/0171960 A1 | 6/2014 | Goode et al. |
| 2014/0188124 A1 | 7/2014 | Lampropoulos et al. |
| 2014/0296905 A1 | 10/2014 | Dela |
| 2014/0350566 A1 | 11/2014 | Emmanouilidis |
| 2014/0350593 A1 | 11/2014 | Laroya et al. |
| 2016/0184576 A1 | 6/2016 | Grace et al. |
| 2016/0184579 A1 | 6/2016 | Triffo |
| 2016/0184580 A1 | 6/2016 | Grace |

FOREIGN PATENT DOCUMENTS

| | | |
|---|---|---|
| EP | 0174930 A1 | 3/1986 |
| EP | 0368568 A2 | 5/1990 |
| EP | 0368568 B1 | 5/1990 |
| EP | 0661949 A1 | 7/1995 |
| EP | 0688184 A1 | 12/1995 |
| EP | 0708621 B1 | 5/1996 |
| EP | 0733382 A2 | 9/1996 |
| EP | 0733383 A2 | 9/1996 |
| EP | 1043042 B1 | 10/2000 |
| EP | 1063926 B1 | 1/2001 |
| EP | 1251787 B1 | 10/2002 |
| EP | 1284782 B1 | 2/2003 |
| EP | 1317214 B1 | 6/2003 |
| EP | 1330194 B1 | 7/2003 |
| EP | 1572282 B1 | 9/2005 |
| EP | 1587573 B1 | 10/2005 |
| EP | 1722696 A1 | 11/2006 |
| EP | 1757234 B1 | 2/2007 |
| EP | 1793886 B1 | 6/2007 |
| EP | 1815811 B1 | 8/2007 |
| EP | 1848497 B1 | 10/2007 |
| EP | 1951350 B1 | 8/2008 |
| EP | 1984056 A1 | 10/2008 |
| EP | 1984072 A2 | 10/2008 |
| EP | 1996089 B1 | 12/2008 |
| EP | 2054116 B1 | 5/2009 |
| EP | 2094178 B1 | 9/2009 |
| EP | 2124766 B1 | 12/2009 |
| EP | 2240126 B1 | 10/2010 |
| EP | 2349026 B1 | 8/2011 |
| EP | 2375997 B1 | 10/2011 |
| EP | 2489313 A1 | 8/2012 |
| EP | 2493392 B1 | 9/2012 |
| EP | 2496151 A2 | 9/2012 |
| EP | 2552327 A1 | 2/2013 |
| EP | 2659841 A2 | 11/2013 |
| EP | 2661233 A1 | 11/2013 |
| EP | 2661288 A1 | 11/2013 |
| EP | 2731513 A1 | 5/2014 |
| EP | 2740437 A1 | 6/2014 |
| EP | 2742871 B1 | 6/2014 |
| EP | 2783658 A2 | 10/2014 |
| EP | 2802276 A1 | 11/2014 |
| WO | 1996028101 A1 | 9/1996 |
| WO | 2001056484 A1 | 8/2001 |
| WO | 2001087412 A2 | 11/2001 |
| WO | 2002022028 A2 | 3/2002 |
| WO | 2005084563 A1 | 9/2005 |
| WO | 2007095252 A1 | 8/2007 |
| WO | 2007100474 A2 | 9/2007 |
| WO | 2008045143 A2 | 4/2008 |
| WO | 2008112608 A2 | 9/2008 |
| WO | 2010002549 A2 | 1/2010 |
| WO | 2011032157 A1 | 3/2011 |
| WO | 2011053645 A1 | 5/2011 |
| WO | 2011123342 A1 | 10/2011 |
| WO | 2012006247 A1 | 1/2012 |
| WO | 2013106713 A1 | 7/2013 |
| WO | 2014080338 A1 | 5/2014 |
| WO | 2014145598 A1 | 9/2014 |

* cited by examiner

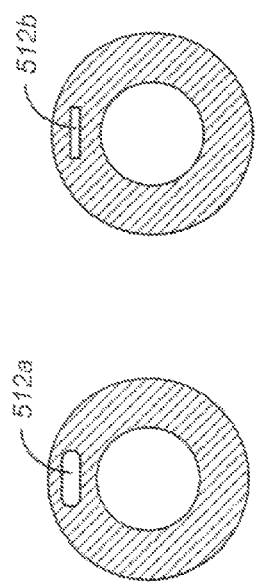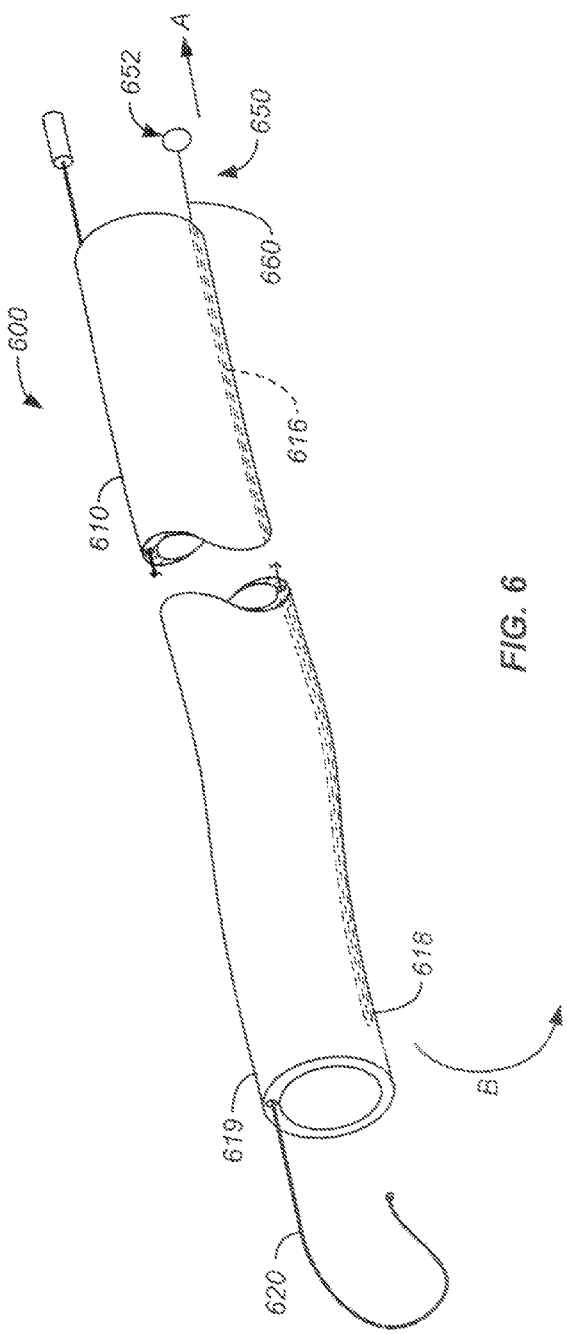

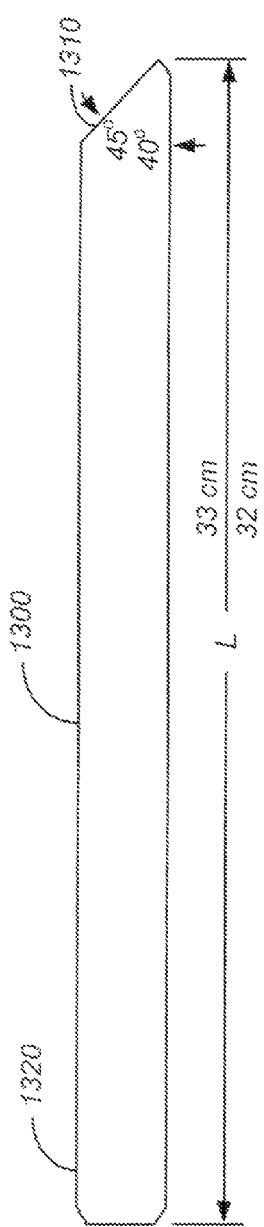
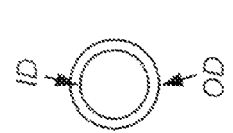
FIG. 13A
FIG. 13B

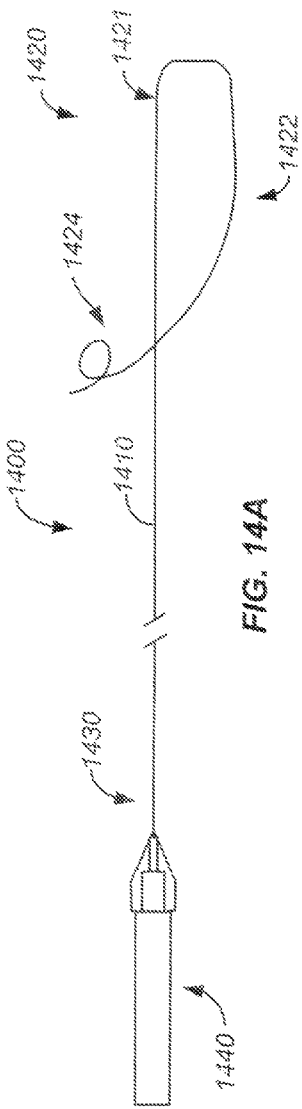
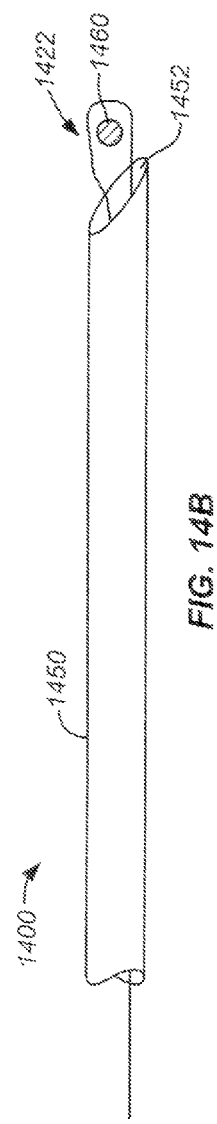
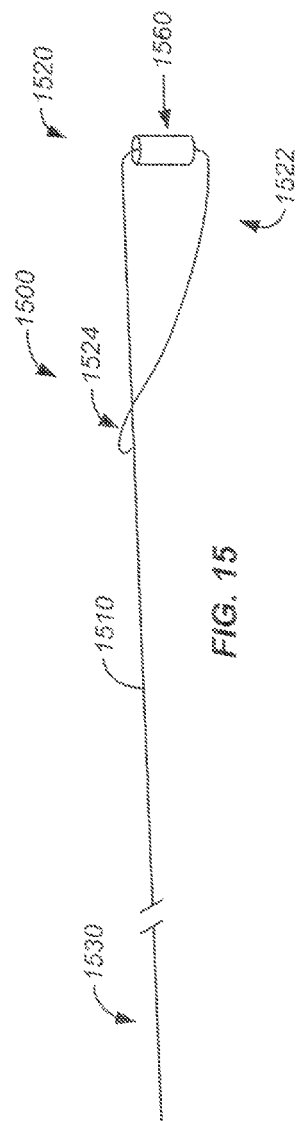
FIG. 14A
FIG. 14B
FIG. 15

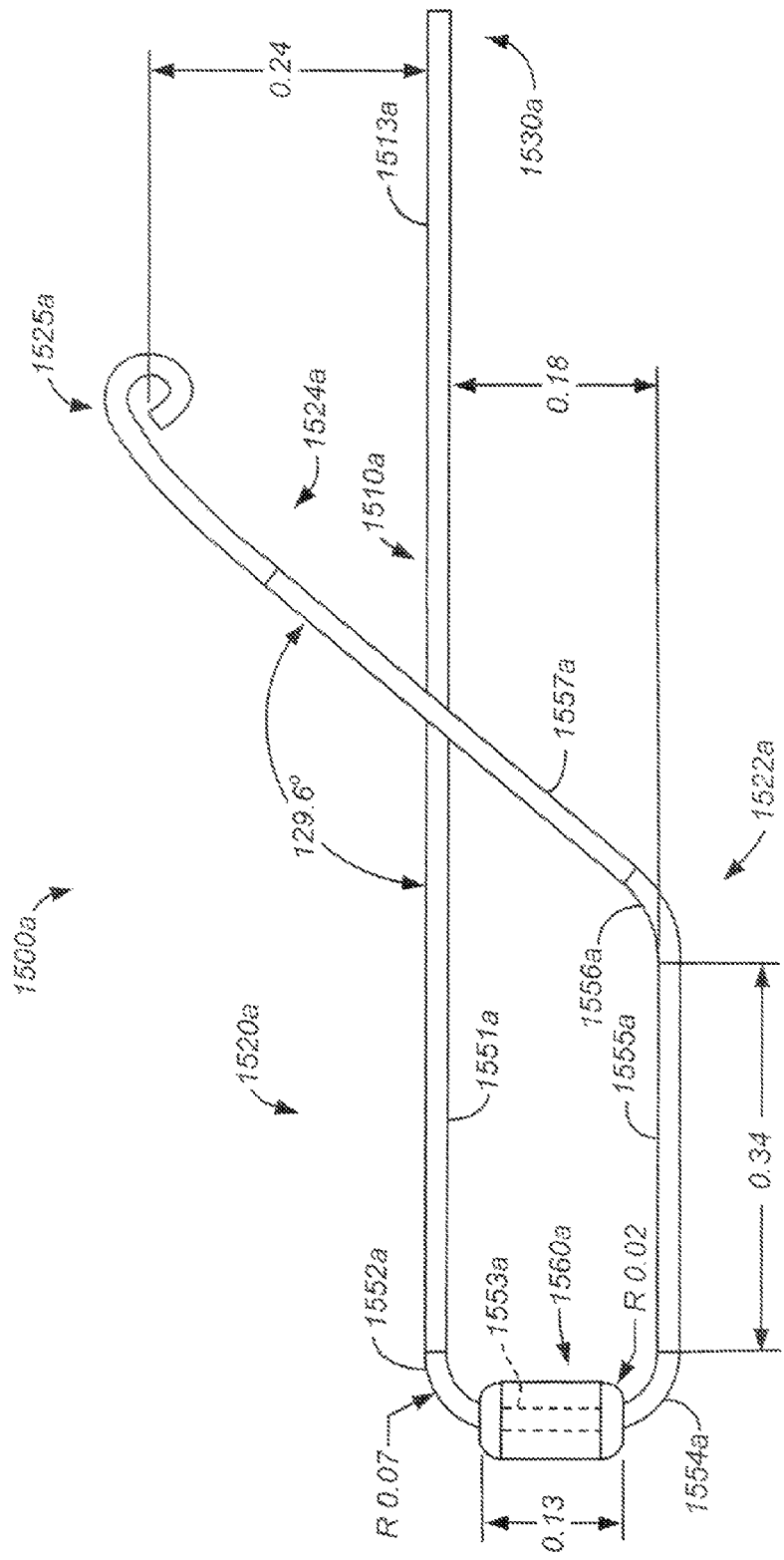

SNARING SYSTEMS AND METHODS

CROSS-REFERENCES TO RELATED APPLICATIONS

This application is a continuation of U.S. patent application Ser. No. 12/878,648, filed Sep. 9, 2010, which is a nonprovisional of and claims the benefit of priority to U.S. Provisional Patent Application No. 61/242,225 filed Sep. 14, 2009. The contents of each of the above applications are incorporated herein by reference for all purposes.

BACKGROUND OF THE INVENTION

Embodiments of the present application relate generally to systems and methods for separating or removing an object from a patient, and more specifically, to techniques for grasping pacing leads within a patient.

A pacemaker can be used to improve heart function in a patient. For example, a pacemaker can transmit electrical signals to the patient's heart, so as to assist the heart to beat in a desired heart rhythm. A pacing system typically includes a pacemaker, a pacing lead, and a controller or processer. A pacing lead often has a wire that transmits electrical impulses to cardiac tissue. Optionally, a pacing lead may transmit information regarding cardiac activity to the pacemaker or processor.

In certain situations, it may be desirable or necessary to remove a pacing lead from a patient. For example, a patient may develop an infection in tissue which is contacting the pacing lead or pacemaker. It may also be advantageous to remove the lead or lead fragment if the lead breaks or otherwise poses a risk of damage, discomfort, or obstruction or interference, if the lead interferes with the operation of another implanted device, or if the patient's vasculature or tissue which is located at or near the lead becomes obliterated or occluded.

In some cases, a lead may develop or present a free end, which can occur when a lead breaks, is pulled out of a header, or is otherwise abandoned during a surgical intervention. If a lead has a free end, it is typically located in the brachiocephalic vein. To remove a lead having a free end, it may be desirable for the physician or operator to navigate the free end of the lead toward an incision site.

Several lead grasping and removal techniques have been proposed. However, some approaches may not be well suited for easily accessing, grasping, or manipulating the free end of a lead. For example, some pig tail catheters may have a limited holding capability, and the lead may slip out of the catheter before it is freed from the patient's anatomy. In certain instances, pig tail catheters can tend to straighten out when pulled by the operator, thus disengaging the lead from the pig tail. Some snares grasp the lead with inappropriate levels of force. Hence, there continues to be a need for improved systems and methods that can simply and effectively grasp and remove a pacing lead or other object from a patient in a reliable manner.

Although some currently proposed treatments may provide real benefits to patients in need thereof, still further advances would be desirable. Embodiments of the present invention provide or intravascular hook or snaring solutions that address the problems which may be associated with the techniques described above, and hence provide answers to at least some of these outstanding needs.

BRIEF SUMMARY OF THE INVENTION

Grasping snares and method for grasping a pacing lead and removing it from the body are disclosed herein. For example, an operator may advance a snaring system through a jugular access site in a patient, providing a relatively non-tortuous pathway to the superior vena cava where the snaring system can be engaged with a pacing lead. Using the snaring system, it is possible to maneuver the pacing lead, which optionally may involve pulling the lead so as to disengage a proximal portion or a distal portion of the lead from an attachment site within the patient. Once a distal or proximal portion of the pacing lead is disengaged, the physician can maneuver the free end toward the access site, by loosely engaging the snaring system with the pacing lead. In some cases, this may involve the use of a snaring system having one or more roller bearings or sleeves. The snaring system can be translated along a length of the pacing lead, and can be used to maneuver or pull a free end of the pacing lead, without transmitting an excessive amount of pulling force or stress on the opposing secured end of the pacing lead.

Advantageously, such grasping snares may be operated with significant pulling forces, while maintaining an engagement with a pacing lead. Exemplary snaring systems include a snare wire with a hooked distal end that is slidable within the wall or lumen of an outer sheath or jacket. Such arrangements permit the distal end of the snare wire to be moved distally away from the outer jacket in order to snare the pacing lead. Once grasped, the pacing lead can be pulled back into the inner lumen of the outer jacket so that it can be withdrawn from the body. Embodiments of the present invention also encompass deflection tendons or bending wires that can be incorporated into the outer jacket to bend or deflect the distal tip of the outer jacket. Embodiments may also include snares having a closed hook at their distal end. A distal end or snare hook may have one or more rotatable bearings. In use, a snare can be inserted into the jugular vein of a patient. The snare can be used to grasp or engage the pacing lead and pull one end out through the jugular vein access site. Once the lead end is extending outside the body, typical lead extraction techniques can be employed. In some cases, grasping snare wires can be extended or advanced through a wall of a catheter body.

Relatedly, embodiments of the present invention encompass systems and methods for snaring or grasping a lead which is disposed within an anatomical location of the patient, such as the jugular vein, the superior vena cava, the right atrium, the right ventricle, the brachiocephalic vein, or the like. Advantageously, the techniques disclosed herein allow a surgeon or operator to effectively grasp, push, pull, twist, rotate, or otherwise maneuver or manipulate an object, such as a pacing lead, within the patient. What is more, snaring systems disclosed herein can withstand high pulling forces without releasing a pacing lead, and can effectively snare a lead in a midsection or central portion, without being threaded over the end of the pacing lead. Exemplary snaring systems allow a pacing lead to slide through a distal hook of a snare wire, without imparting high forces to the pacing lead or adhered vasculature. Features such as a hook tag end and a bent or shaped snare wire allow an operator to effectively steer or navigate the snare system to the pacing lead for capture. Moreover, snaring systems disclosed herein are easily releasable from the pacing lead. In some cases, snaring systems can include a hook or snare that can hook and retain a pacing lead, and pull a portion of the pacing lead downward toward the femoral vein or upward toward the jugular vein and out of the access site. Systems can also allow the pacing lead to move through a snare wire or catch mechanism as the lead is being pulled or during the snaring process. Exemplary embodiments can also release a hook or snare if the procedure is not successful or is interrupted.

In one aspect, embodiments of the present invention encompass snaring systems and methods for engaging an object within a patient's body. An exemplary snaring system includes an elongate element having a proximal end and a distal end. The distal end can include a loop. The system also includes an outer sheath having a central lumen. The central lumen can be configured to receive at least a portion of the loop of the distal end of the elongate element. In some cases, a system may also include a rotatable bearing in operative association with the loop of the distal end of the elongate element. The distal end of the elongate element can include a tag, and the central lumen of the outer sheath can be configured to receive the tag. In some embodiments, the outer sheath includes a second lumen extending through a side wall of the sheath, and the second lumen is configured to receive at least a portion of the elongate element.

In some cases, the elongate element includes a flattened portion, a square cross section portion, or a rectangular cross section portion. Optionally, the system may include a deflection mechanism coupled with the outer sheath.

In another aspect, embodiments of the present invention encompass systems and methods for engaging a pacing lead disposed within a patient. An exemplary method includes inserting a snaring system through a jugular or femoral access site of a patient, engaging a pacing lead with the snaring system, sliding the snaring system along a length of the pacing lead so as to move a portion of the pacing lead toward the jugular or femoral access site of the patient, and withdrawing the snaring system from the jugular or femoral access site so as to remove at least a portion of the pacing lead from the patient. In some cases, the step of engaging the pacing lead can include engaging the pacing lead with a roller mechanism of the snaring system. In some cases, the step of engaging the pacing lead can include engaging the pacing lead with a capture mechanism of the snaring system. Optionally, the capture mechanism of the snaring system can include an elongate element having a loop. In some cases, the step of engaging the pacing lead can include sliding the elongate element along a side wall lumen of a catheter of the snaring system.

In a further aspect, embodiments of the present invention encompass systems and methods for engaging an object disposed within a patient. An exemplary method may include inserting a snaring system through an access site of a patient. The snaring system can include an elongate element having a distal loop and a rotatable roller mechanism disposed along the distal loop of the elongate element. The method may also include engaging the object with rotatable roller mechanism of the snaring system, and withdrawing the snaring system toward the access site so as to move at least a portion of the object toward the access site. In some cases, the elongate element may include a tag end that is disposed distal to the rotatable roller mechanism. The rotatable roller mechanism may include a bearing having a tubular shape. Optionally, the rotatable roller mechanism may include a bearing having a spherical shape. In some cases, the rotatable roller mechanism includes a first cylindrical bearing defining a first central longitudinal axis and a second cylindrical bearing defining a second central longitudinal axis. The first central longitudinal axis can be angularly offset from the second central longitudinal axis. In some instances, the first central longitudinal axis is angularly offset from the second central longitudinal axis by about 90 degrees.

In still another aspect, embodiments of the present invention encompass a snaring system for engaging an object within a patient's body, which includes an elongate element having a proximal end and a distal end. The distal end of the elongate element can include a loop and a tag. The snaring system may also include a rotatable bearing in operative association with the loop of the distal end of the elongate element. In some cases, the rotatable bearing is disposed on a first section of the loop, and the loop has a second section distal to the first section and a third section proximal to the first section, such that the second section and the third section are in substantial parallel alignment. In some cases, the first section is in substantial perpendicular alignment with each of the second section and the third sections.

For a fuller understanding of the nature and advantages of the present invention, reference should be had to the ensuing detailed description taken in conjunction with the accompanying drawings.

BRIEF DESCRIPTION OF THE DRAWINGS

FIGS. 5A and 5B illustrate aspects of a grasping snare system according to embodiments of the present invention.

FIG. 6 illustrates aspects of an object removal or snaring system according to embodiments of the present invention.

FIGS. 13A and 13B depict aspects of a snaring system according to embodiments of the present invention.

FIGS. 14A and 14B depict aspects of a snaring system according to embodiments of the present invention.

DETAILED DESCRIPTION OF THE INVENTION

In certain surgical situations, a patient may present with a pacing lead that is no longer disposed within the pocket, but instead is freely floating in the brachiocephalic vein, the superior vena cava, the right atrium, or the like. Embodiments of the present invention provide techniques for grasping a free end of the pacing lead and maneuvering or pulling it toward the jugular vein. Exemplary approaches provide removal or snare systems that can hook, grasp, push, pull, and twist a pacing lead. Such advances allow an operator may degrees of freedom when removing a lead having a free end.

According to embodiments of the present invention, techniques may include pulling the free end of the lead down from the femoral vein using a femoral vein approach. Once the lead is located within the right atrium or inferior vena cava, the physician can use a snare device inserted through the jugular vein to grasp or engage the lead and pull it toward an opening or incision in the jugular vein. The free end of the lead can be pulled back up through the jugular vein, via the inferior vena cava, right atrium, and superior vena cava. In some cases, this technique can involve using a first snare to hook the lead and pull the lead down through the inferior vena cava and into the femoral vein. The technique can also involve using a second snare to grasp or engage the end of the lead from a jugular access site, and pull the free end up through the jugular access site. Optionally, a laser sheath or other removal device can then be used over the lead to free or dislodge the distal end of the lead for removal.

Figure 1A:
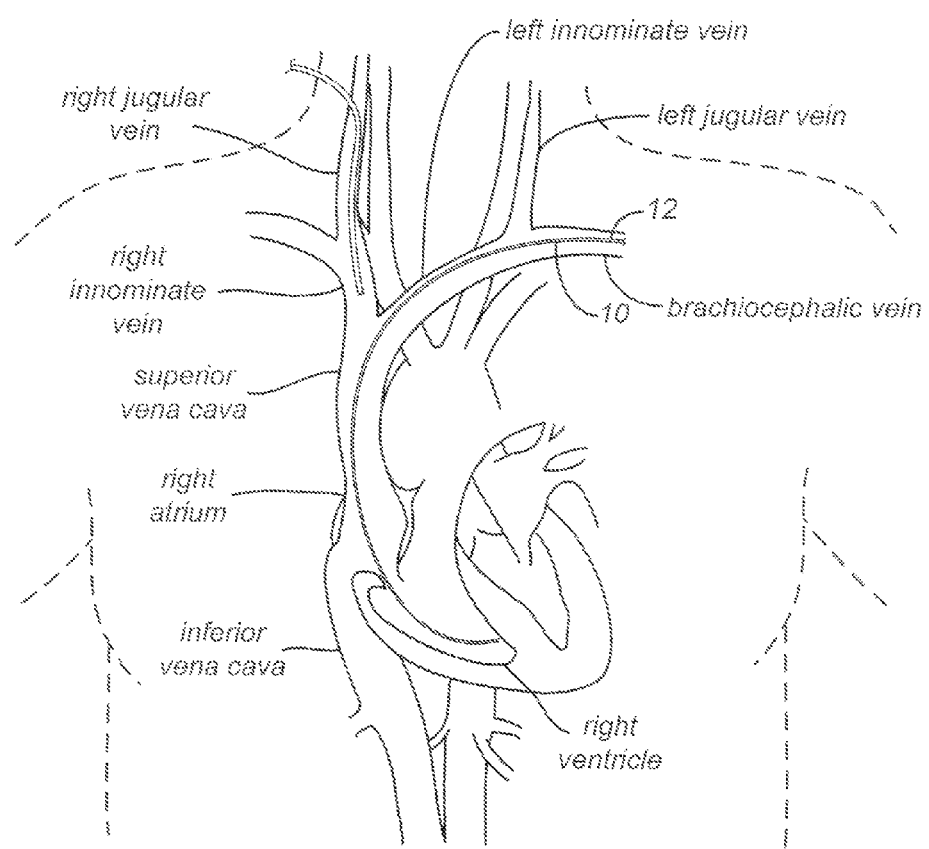
FIGS. 1A to 1F illustrates aspects of object grasping or removal systems and methods according to embodiments of the present invention.
Figure 1B:
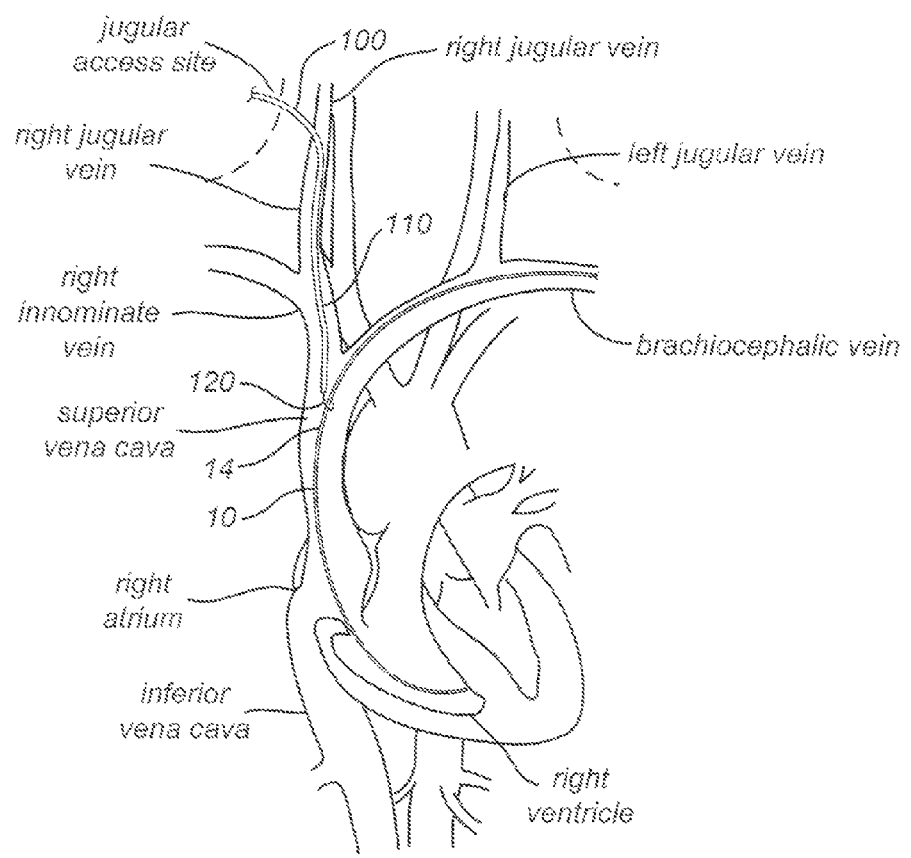

Turning now to the drawings, FIGS. 1A to 1F illustrates aspects of an object grasping or removal system 100 according to embodiments of the present invention. FIG. 1A shows a pacing lead 10 disposed within a patient's body, such that a free end 12 of the lead is floating freely within the brachiocephalic vein. As depicted in FIG. 1B, an object grasping or removal system 100 can be advanced within the jugular vein, and then used to snare, grasp, hook, or otherwise engage the pacing lead. In some cases, grasping or removal system 100 is used to grasp or engage pacing lead 10 at or near a central portion 14 of the pacing lead. Optionally, grasping or removal system 100 can be used to grasp or engage a portion of pacing lead 10 which is disposed at or near the right atrium, or at or near the superior vena cava. As shown here, object grasping or removal system 100 includes an outer sheath 110 and a catch mechanism 120. The catch mechanism is extended from the outer sheath, so that it may contact, hook, or engage the pacing lead.

Figure 1C:
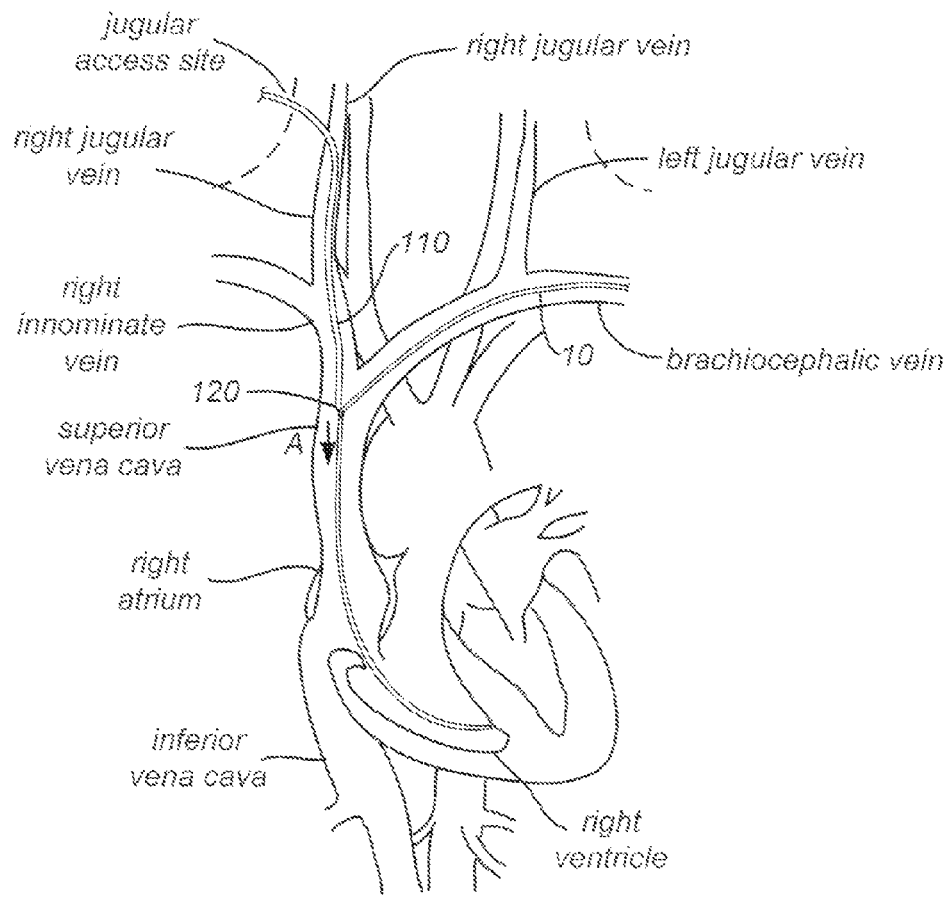
Figure 1D:
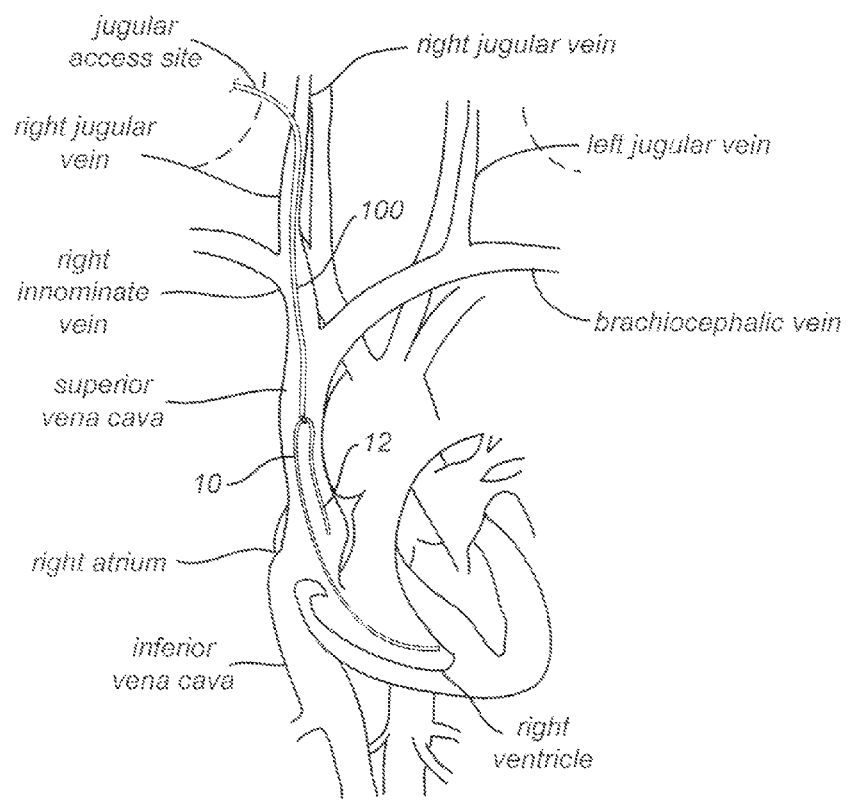

As illustrated in FIG. 1C, catch mechanism 120 can be activated, for example by withdrawing it into outer sheath 110, so as to capture, secure, or engage the pacing lead. While pacing lead 10 is engaged or firmly held by grasping or removal system 100, the operator may manipulate the removal system so as maneuver the pacing lead as desired. In some cases, it may be desirable or beneficial for the physician to administer a pulling action, wherein the pacing lead is not firmly grasped by the snaring system, but instead is more loosely engaged by the snaring system, such that he snaring system allows movement of the pacing lead through a snaring loop of the system during withdrawal of the lead. As shown in FIG. 1C, the operator can push grasping or removal system 100 into or toward the right atrium, in the direction illustrated by arrow A, thus advancing the pacing lead into or toward the right atrium. Subsequently, free end 12 of pacing lead 10 is withdrawn from the brachiocephalic vein and into or near the right atrium, as illustrated in FIG. 1D. Although FIG. 1D illustrates the situation where a proximal portion of the pacing lead becomes freed, embodiments of the present invention also encompass situations where instead, or in addition, a distal portion of the pacing lead becomes freed. For example, when physician uses the snaring system to pull on the pacing lead, the distal end of the pacing lead may become dislodged or separated from the cardiac tissue.

Figure 1E:
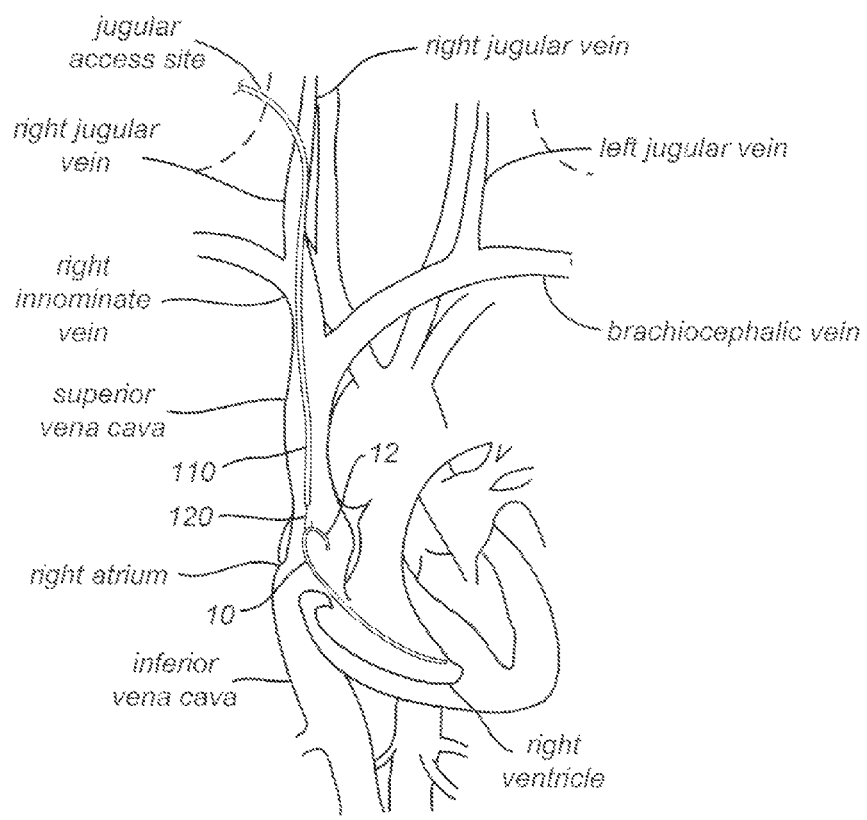

The surgeon may adjust the positioning of the object grasping or removal system on the pacing lead. For example, as shown in FIG. 1E, catch mechanism 120 can be released or relaxed, for example by extending it from outer sheath 110. Hence, the catch mechanism is in an open configuration, and the grasping or object removal system can be repositioned as desired at another location along the pacing lead. In the embodiment shown here, grasping or object removal system is repositioned toward free end 12 of pacing lead 10. In some cases, the operator may slide the grasping or removal system along the pacing lead to achieve the desired repositioning.

Figure 1F:
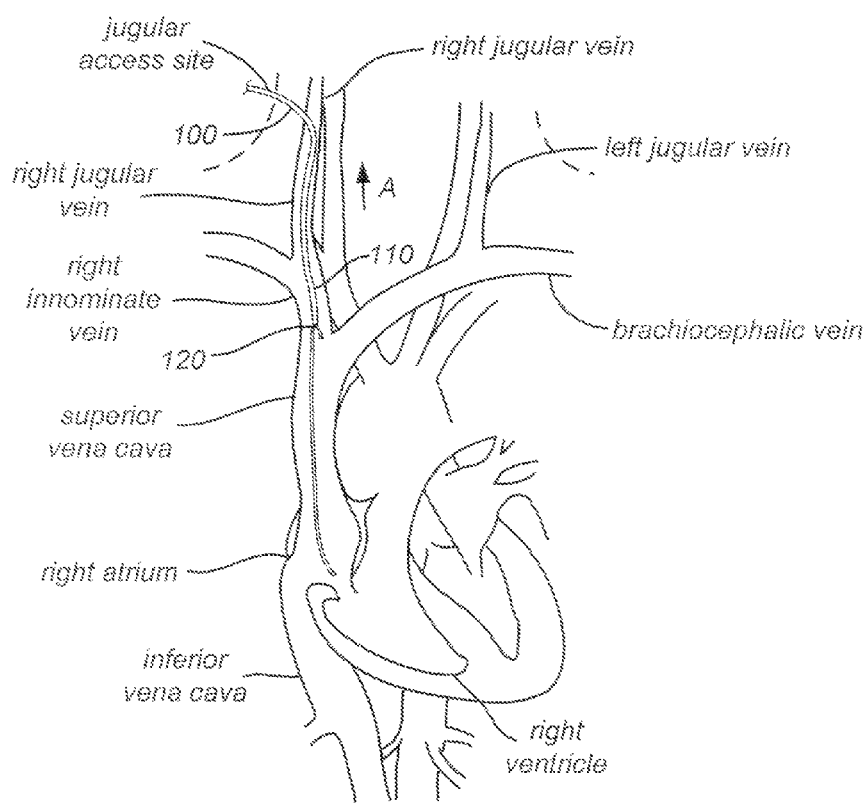

When the grasping or removal system is in the appropriate location relative to the pacing lead, the operator may activate catch mechanism 120 so as to firmly secure or grasp pacing lead 10 with removal system 100, as shown in FIG. 1F. The operator may then pull or withdraw the pacing lead through the jugular vein, and toward a jugular access site, in direction indicated by arrow A. The operator may then use the jugular access site to pass a laser sheath or other lead removal device along grasping or removal system 100.

Figure 2:
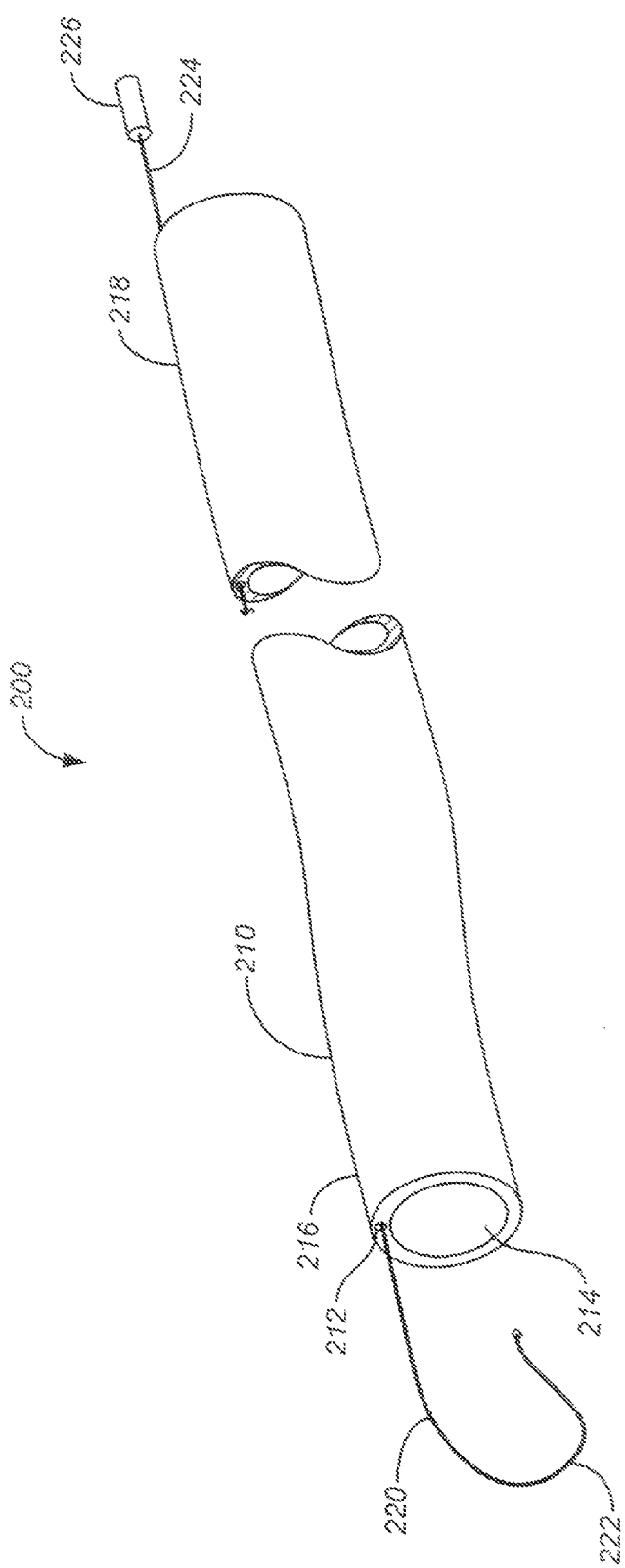
FIG. 2 illustrates aspects of an object removal system or grasping snare according to embodiments of the present invention.

As shown in FIG. 2, an object removal system or grasping snare 200 can include an outer sheath 210 such as a jacket or tube, and a catch mechanism 220 such as an snare wire. In some cases, catch mechanism 220 includes an internal wire having a distal hook. The internal wire can run along a length of the tube, and the wire can be configured to move axially within the tube. For example, in some cases the wire can slide along an inner wire lumen 212 of the tube. The distal end 222 of the wire 220 which includes the hook can also be received or disposed within a catch lumen 214 of the tube. For example, in some cases the distal hook can be extended from a distal portion 216 of the tube, and retracted back toward or into the tube. The wire can have a proximal end 224, which extends from a proximal portion 218 of tube 210, that includes a loop or pull mechanism 226 such as a pull or torque handle. Outer jacket or tube 210 can be used by the operator to support or carry snare wire 220, and to provide push, pull, and rotation movements.

Figure 3A:
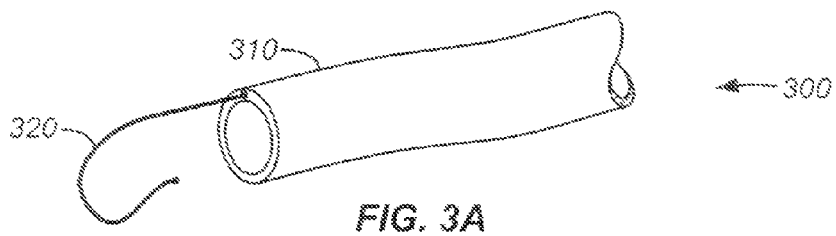
FIGS. 3A to 3D illustrate aspects of an object removal system or grasping snare according to embodiments of the present invention.
Figure 3B:
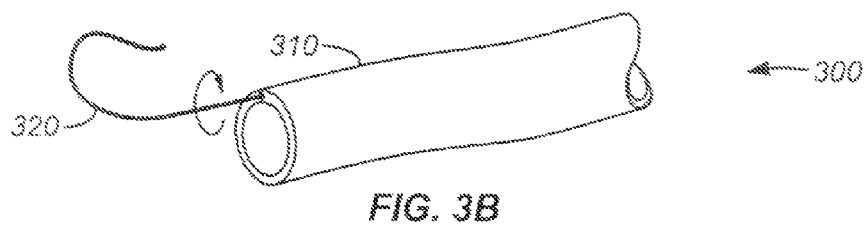
Figure 3C:
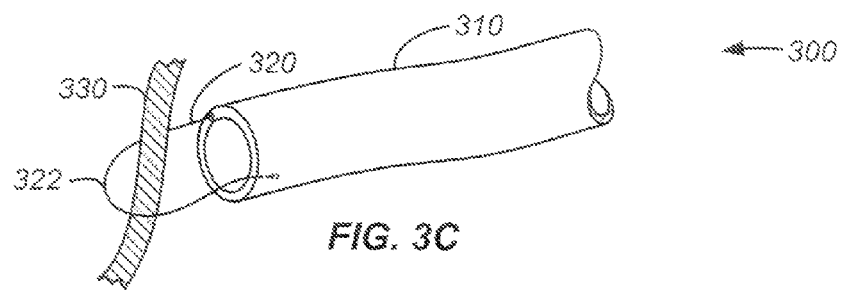
Figure 3D:
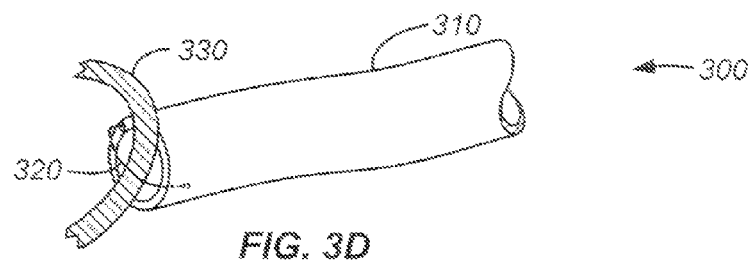

In operation, the physician can use the distal hook of the wire, for example when it is extended from the tube, to grasp or snare the free lead. For example, FIG. 3A illustrates an object removal system or grasping snare 300 having an outer tube 310 and a snare wire 320. The catch mechanism or snare wire 320 is in an open position. FIG. 3B also shows snare wire 320 in an open position, wherein the snare wire is rotated about 180 degrees relative to the configuration shown in FIG. 3A. A distal hook 322 can assist in functioning as a grasping snare or a hook snare. When a pacing lead 330 is disposed within hook 322, the operator can pull the snare wire toward the outer tube, as shown in the closing position or configuration depicted in FIG. 3C. When the pacing lead is engaged with or corralled by the hook, the hook can be moved along a length of the pacing lead, or the hook can be used to maneuver the positioning of the pacing lead, without applying a significant pulling or pushing force to the pacing lead, or to an affixed or embedded portion of the pacing lead. What is more, the operator can pull snare wire 320 further into tube 310, thus firmly grasping the lead, as shown in the closed position or configuration depicted in FIG. 3D. The grasping snare 300 can then be used to push, pull, twist, or otherwise maneuver pacing lead 330. To release the lead, the operator can extend the distal hook of the wire from the tube, for example by pushing it forward relative to the tube, thus exposing the hook.

Figure 4A:
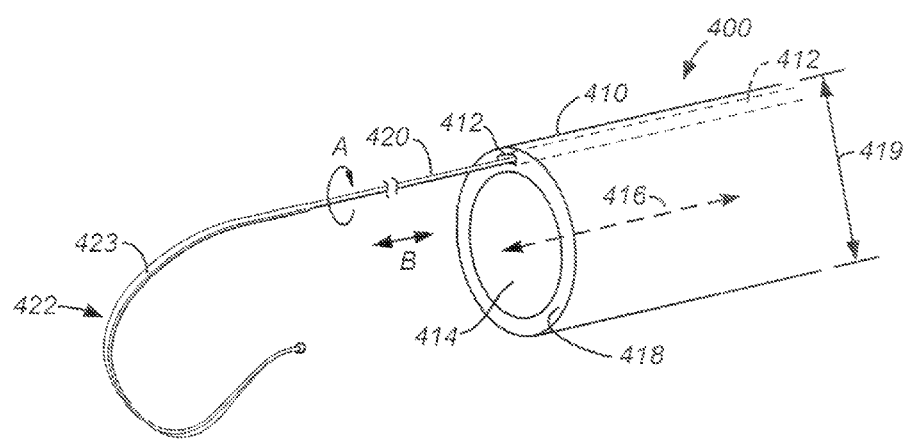
FIGS. 4A and 4B illustrate aspects of a grasping snare system according to embodiments of the present invention.
Figure 4B:
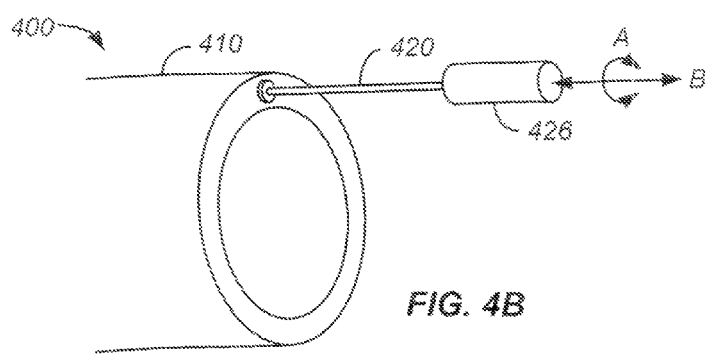

As illustrated in the embodiment depicted in FIG. 4A, grasping snare system 400 can include an outer tube 410 and an inner snare wire 420. Snare wire 420 can be rotated relative to tube 410 as indicated by arrow A, optionally via rotation of a wire handle 426 as indicated by arrow A shown in FIG. 4B. Relatedly, snare wire 420 can be translated relative to tube 410 as indicated by arrow B shown in FIG. 4A, optionally via translation of wire handle 426 as indicated by arrow B shown in FIG. 4B. In some cases, snare system 400 can include a seal disposed toward a proximal end of tube 410, or a luer fitting that accepts a rotating hemostasis valve.

As shown in FIG. 4A, tube or outer jacket 410 of snare system 400 may have two lumens, for example a wire lumen 412 and a capture lumen 414. According to some embodiments, wire lumen 412 can be laterally offset from a central longitudinal axis 416 of the outer jacket. For example, wire lumen 412 can be disposed within a wall 418 of jacket 410. According to such configurations, snare wire 420 can be constrained to or contained within one side of the tube. Such tube configuration can also allow a distal hook 422 of the wire to be rotated outside the axis or silhouette defined by the outer diameter 419 of the tube, so as to provide a larger snaring area. Wire lumen 412 within the tube can present a slot configuration. For example, as shown in FIG. 5A, wire lumen 512a can present an oval shaped cross section. Relatedly, as shown in FIG. 5B, wire lumen 512b can present a square or rectangular shaped cross section.

Such shaped inner wire lumens 512a, 512b can be formed during an extrusion process, or reformed with an insert. Relatedly, the snare wire can include a shaped portion, which presents a similarly shaped ovular or rectangular profile. For example, as depicted in FIG. 4A, it is possible to provide a flattened portion 423 at or near the distal curve section 422 of the snare wire 420 to key it into the lumen or slot 412 in the side or wall of outer jacket 410. In this way, snare wire 420 can be keyed with tube 410. Such modifications can increase the surface area on the outer or top portion of the loop 422 to prevent or inhibit snare wire 420 from cutting into or stripping the pacing lead. Hence, a flattened or shaped portion can be placed on the distal section of the wire to key the snare wire to the tube. A section of the wire proximal to the flattened or shaped portion can be round or rounded in shape, so as to allow the snare wire to be rotated relative to the tube within the inner wire aperture, when the flattened or shaped section is distal to the tube lumen. In addition to flattened shapes, the snare wire and slot 412 may present square cross-section shapes, rectangular cross-section shapes, and other complementary interlocking or keyed shapes. In some embodiments, such keyed snaring systems may include roller bearings or sleeves as described elsewhere herein, for example with reference to FIGS. 9 to 11C, and 15 to 15C.

According to some embodiments, snare wire 420 or loop area 422 can include a slip coating or reduced friction surface, to allow the snare to slide along the lead, for example when the snare is being opened or closed. In some cases, such a coating or surface can include PTFE, Teflon, Teflon spray, paralene, or any suitable reduced-friction spray, tubing, coating, or solution.

Outer jacket or tube 410 can be constructed of one or materials including Pebax, ABS, PEEK, FEP, PE, Nylon, a Pebax braid matrix, or the like. The outer diameter (OD) of the tube can be within a range from about 0.090 inches to about 0.160 inches. In some cases, the outer diameter of the tube can be sized so as to allow a laser sheath, which may be 12Fr to 16Fr, to pass over the snaring assembly. For example, the outer diameter can be sized to allow a 12Fr laser sheath pass over the tube 410. The snare wire can be constructed of one or more materials such as stainless steel, NiTi, or the like. The outer diameter (OD) of the wire can be within a range from about 0.010 inches to about 0.050 inches. The wire can be configured to provide sufficient strength to pull on a pacing lead while providing sufficient flexibility to navigate the patient's anatomy.

As shown in FIG. 6, embodiments of the present invention encompass mechanisms that can deflect a distal end of the outer tube. Snaring system 600 includes an outer tube 610, a snare wire or capture mechanism 620, and a deflection mechanism 650. The deflection mechanism may include, for example, a pull wire or a steering tendon 660. Deflection mechanism 650 can provide to the snare system an additional degree of freedom while manipulating the snare system to grasp a pacing lead. In some cases, a deflection mechanism can include a tendon wire that is housed in a wall of outer tube 610, for example within a deflection mechanism lumen 616, and anchored at some point distal, for example at an anchor point 618. According to some embodiments, the location of anchor point 618 along the length of tube 610 can be determined by the radius of curvature desired during operation of the deflection mechanism. For example, as the anchor point is located more closely to a distal end 619 of tube 610, it is possible to achieve a bend in tube 610 having a smaller radius of curvature when actuating the deflection mechanism. According to some embodiments, anchor point 618 can be located within 20 cm of the distal end of tube 610. In some cases, anchor point 618 may include an embedded eyelet or an anchor band. Anchor point 618 can serve to fix a distal portion of the pull wire relative to the outer tube.

As depicted in FIG. 6, deflection can be effected by applying tension to a proximal end 652 of the tendon wire, for example by pulling the wire in the direction indicated by arrow A, which in turn causes the distal end of the tube to deflect in the direction indicated by arrow B. The tendon wire can have a diameter within a range from about 0.005 inches to about 0.030 inches, according to some embodiments. The tension can be applied by through the use of a mechanical mechanism or through the use of manual force provided directly by the user. In some cases, a mechanical deflection mechanism can include a screw, a cam or cylindrical disk, a lever, or other mechanical means to tension a wire. A mechanical deflection mechanism could be mounted in a housing to create a handle. According to some embodiments, a handle can be configured to lock the tube in a deflected configuration as desired during a surgical procedure, and until the operator unlocked the tube from the deflected orientation.

According to some embodiments, a snare system may include a pre-shaped outer tube that can be straightened or shaped by advancing a straight or shaped mandrel through a lumen in the wall of the outer tube. The degree of straightening, or deflection, can be controlled by the distance or extent to which the mandrel is advanced distally into the wall or lumen of the outer tube. In some cases, a mandrel can be integrated with the outer tube, yet allow it to be slidable. In some cases, a mandrel can be an auxiliary member that is removable. A distal end of the mandrel can be made with a ball-end tip to prevent or inhibit it from perforating the outer tube when it is advanced.

Snaring systems which include shaped wire element such as those depicted in FIGS. 2, 3A to 3D, 4A, and 6 are well suited for loosely engaging and maneuvering a pacing lead without subjecting the pacing lead to significant pulling forces. Such systems are particularly useful in pacing lead removal methods such as those described herein with reference to FIGS. 7A and 7B. For example, in some cases, it may be desirable or beneficial for the physician to administer a pulling action, wherein the pacing lead is not firmly grasped by the snaring system, but instead is more loosely engaged by the snaring system, such that the snaring system allows movement of the pacing lead through a snaring loop of the system as the system is navigated or manipulated by the physician.

Figure 7A:
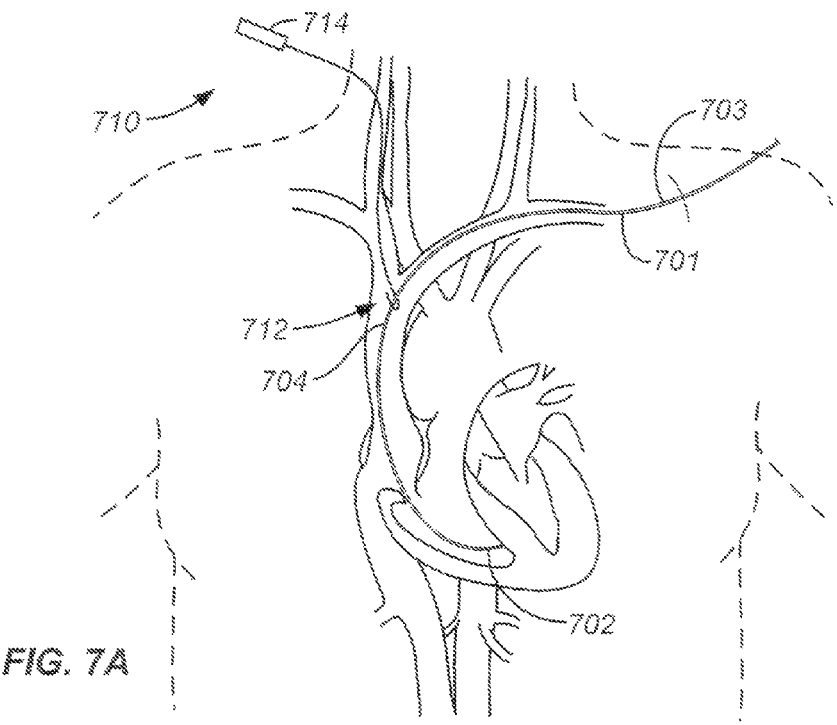
FIGS. 7A and 7B illustrates aspects of pacing lead snaring or removal systems and methods according to embodiments of the present invention.

As noted above, exemplary lead extraction procedures can involve a femoral or jugular approach to accessing or removing the lead, in contrast to a superior or lead pocket approach. FIG. 7A illustrates aspects of a lead snaring or removal process, according to embodiments of the present invention. As depicted here, pacing lead 701 is disposed within the patient, such that a distal portion 702 of pacing lead 701 is secured in the patient's right ventricle. A proximal portion 703 of pacing lead is disposed at or near the pacemaker pocket of the patient. Snaring system 710 can be used to snare, grasp, or otherwise engage the pacing lead. For example, an elongate element or hooked wire of the snaring system can be inserted into the vasculature through a snaring system sheath, either from a jugular vein or femoral vein access site. The distal hook or loop can be placed near the pacing lead at or near the vicinity of the superior vena cava. A distal loop 712 of snaring system 710 can be used to hook a central portion 704 of the pacing lead, optionally by maneuvering or manipulating a control handle 714 of the snaring system. For example, the snaring wire can be rotated via a handle or pin vice 714 so that a hook tag end of distal portion 712 catches the lead. The operator can pull up on the snare wire or snaring system to cause the pacing lead to slide into the enclosed area of the distal hook.

Figure 7B:
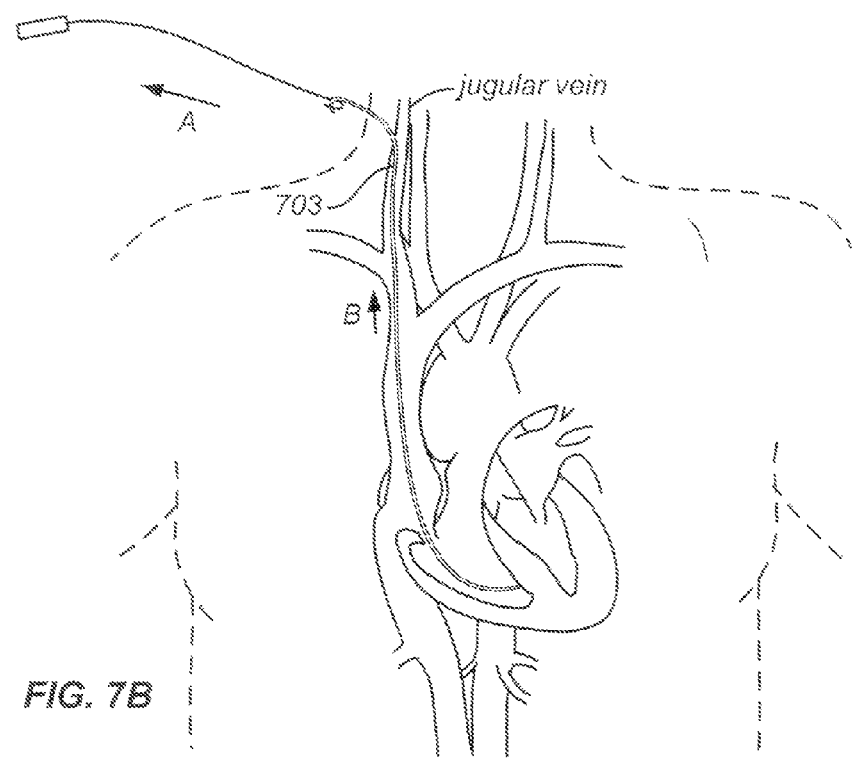

As shown in FIG. 7B, when the distal loop or hook 712 of snaring system 710 has caught the pacing lead, the snaring system can be retracted or pulled up in the direction indicated by arrow A, so as to withdraw proximal portion 703 of the pacing lead away from the pacemaker pocket, and into the jugular vein. During withdrawal of the snaring system, distal loop 712 of the snaring system can slide along a length of the pacing lead, from central portion 704 toward proximal portion 703, as indicated by arrow B. Although FIGS. 7A and 7B illustrate the situation where a proximal portion of the pacing lead becomes freed, embodiments of the present invention also encompass situations where instead, or in addition, a distal portion of the pacing lead becomes freed. For example, when physician uses the snaring system to pull on the pacing lead, the distal end of the pacing lead may become dislodged or separated from the cardiac tissue.

Optionally, as discussed elsewhere herein, a sheath can be placed over the snaring wire and advanced over the tag end of the distal hook, so as to cinch or secure the pacing lead to the snaring system. The sheath and snaring wire can then be pulled to free the proximal portion of the pacing lead. Once free, the snaring wire and sheath can be pulled out of the body access site along with the proximal end of the pacing lead. With the proximal end of the pacing lead disposed outside of the body, the entire pacing lead can be extracted via lead extraction techniques, for example via laser lead extraction. To disengage the snaring system from the pacing lead, the operator can push and rotate the snaring wire to release the hook from the pacing lead.

Figure 8:
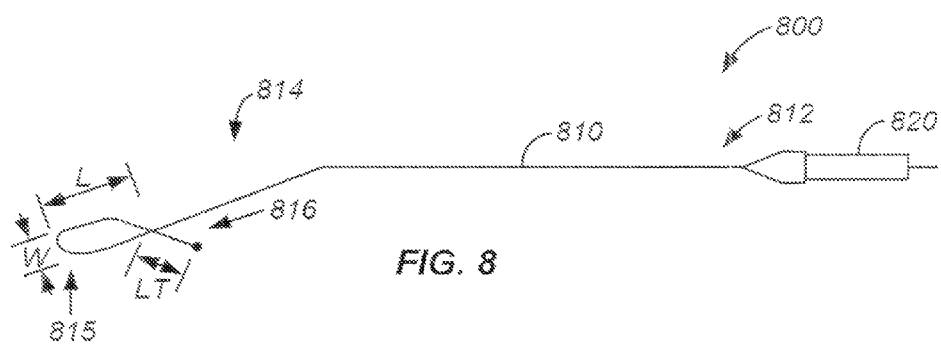
FIG. 8 depicts aspects of a snaring system according to embodiments of the present invention.

FIG. 8 depicts a snaring system 800 according to embodiments of the present invention. Snaring system 800 includes an elongate element or wire 810 having a proximal portion 812 and a distal portion 814. System 800 can include a pin vice or handle 820 coupled with proximal portion 812 of elongate element 810. As shown here, distal portion 814 of elongate element 810 includes a looped or hooked portion 815. Distal portion 814 can also include a tag end 816. According to some embodiments, elongate element 810 includes a stainless steel wire having a diameter of about 0.020 inches. Looped portion 815 can have a length L of about 0.5 inches and a width W of about 0.2 inches. In some cases, tag end 816 can have a length LT of about 0.25 inches. In some cases, tag end 816 can have a length LT of about 0.50 inches.

Figure 9:
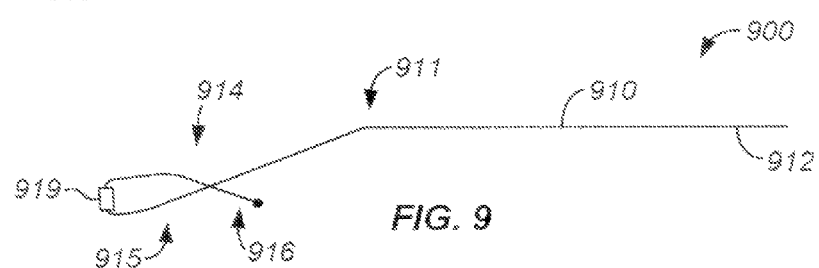
FIG. 9 depicts aspects of a snaring system according to embodiments of the present invention.
Figure 10:
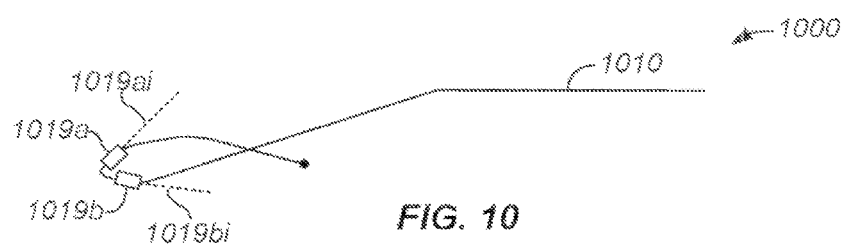
FIG. 10 depicts aspects of a snaring system according to embodiments of the present invention.
Figure 11:
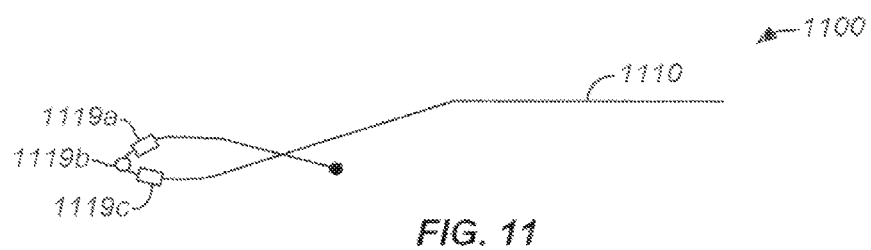
FIGS. 11 to 11C depict aspects of a snaring system according to embodiments of the present invention.

FIG. 9 depicts a snaring system 900 according to embodiments of the present invention. Snaring system 900 includes an elongate element or wire 910 having a proximal portion 912 and a distal portion 914. System 900 can include a handle 920 coupled with proximal portion 912 of elongate element 910. As shown here, distal portion 914 of elongate element 910 includes a looped or hooked portion 915. Distal portion 914 can also include a tag end 916. System 900 further includes a bearing or sleeve 919 disposed about a section of distal portion 914. In some cases, bearing 919 can rotate about elongate element 910. Bearing 919 can provide reduced friction between elongate element 910 and a pacing lead. Elongate element 910 can include one or more bends 911 which can enhance steerability of the snaring system. A bearing element can include a metal material, such as stainless steel, titanium, or the like. In some cases, a bearing element may include a plastic material, such as Teflon, nylon, polycarbonate, high-density polyethylene (HDPE), ultra high molecular weight polyethylene (UHMWPE), or the like. A bearing or sleeve can have a cylindrical or tubular shape. For example, a bearing can present a cylindrical shape, having a diameter with a range from about 0.04 inches to about 0.12 inches. FIG. 10 illustrates a snaring system 1000 which includes two bearings or sleeves 1019a, 1019b disposed about an elongate element 1010. As shown here, bearing or sleeve 1019a may define, for example by way of an internal lumen, a central longitudinal axis 1019ai, and bearing or sleeve 1019b may define, for example by way of an internal lumen, a central longitudinal axis 1019bi. Axis 1019ai may be angularly offset from axis 1019bi. FIG. 11 illustrates a snaring system 1100 which includes three bearings or sleeves 1119a, 1119b, 1119c disposed about an elongate element 1110. One or more of the bearings may present a spherical shape. For example, bearing 1119b can present a spherical shape having a diameter within a range from about 0.04 inches to about 0.10 inches. Snaring systems having roller bearings or sleeves can allow a physician to apply significant pulling forces to the catheter, while still maintaining an operable engagement between the snaring system and the pacing lead. The roller bearing or sleeve can act to dissipate a portion of the applied force, such that a reduced amount of force is applied to the pacing lead itself.

As depicted in FIG. 8, elongate element 810 can have a radiused bottom or distal looped portion. Relatedly, as depicted in FIG. 9, elongate element 910 can have a straight bottom or distal looped portion. As shown in FIG. 10, elongate element 1010 can have an angled bottom or distal looped portion, such that a first straight section is angularly offset from a second straight section by about 90 degrees. Accordingly, the snaring system, which presents two roller bearings 1019a, 1019b that can simultaneously contact a pacing lead, provides roller bearings edges that are angularly offset from one another by about 90 degrees. As shown in FIG. 11, elongate element Ill 0 can have an angled bottom or distal looped portion, such that a first straight section is angularly offset from a second straight section by about 90 degrees. Accordingly, the snaring system, which presents three roller bearings 1119a, 1119b, 1119c that can simultaneously contact a pacing lead, provides cylindrical roller bearings edges that are angularly offset from one another by about 90 degrees. Typically, the bottom or distal looped portions are appropriately sized to accommodate a pacing lead. For example, as shown in FIG. 8, in some cases a bottom or distal looped portion may have a length L that is about twice as long as a width W. To accommodate a large defibrillator lead having a diameter of about 0.170 inches, for example, the looped or hooked portion 815 may have a length L of about 0.5 inches and a width W of about 0.2 inches. In some cases, the incorporation of an increased number of rollers or bearings, for example as depicted in FIG. 11, allows the operator to pull the snaring system along a pacing lead using a correspondingly reduced amount of force.

Snaring systems which include a roller bearing or sleeve as described herein are well suited for loosely engaging and maneuvering a pacing lead without subjecting the pacing lead to significant pulling forces. Such systems are particularly useful in pacing lead removal methods such as those described herein with reference to FIGS. 7A and 7B. For example, in some cases, it may be desirable or beneficial for the physician to administer a pulling action, wherein the pacing lead is not firmly grasped by the snaring system, but instead is more loosely engaged by the snaring system, such that he snaring system allows movement of the pacing lead through a snaring loop of the system as the system is navigated or manipulated by the physician.

Hence, snare systems can include a closed hook and tag end which can be used to grab a pacing lead or otherwise allow the pacing lead entry into the hook. An elongate element or wire may include a medical grade wire constructed of stainless steel, Nitinol, or the like. The elongate element or wire can be tapered from a larger diameter on a proximal portion or end to smaller diameter on a distal portion or end, and may have varying diameters along the length of the wire to add flexibility or strength where needed or desired. The construction can also include a central core mandrel, which may also be tapered or of varying diameter, which in turn is covered with a coil. A tag end may present an atraumatic configuration. In some cases, a tag end may terminate in a ball end. In some cases, a tag end may terminate in a pig tail configuration or a flexible coil. Atraumatic configurations can help to prevent or inhibit perforation of the vasculature.

Figure 11A:
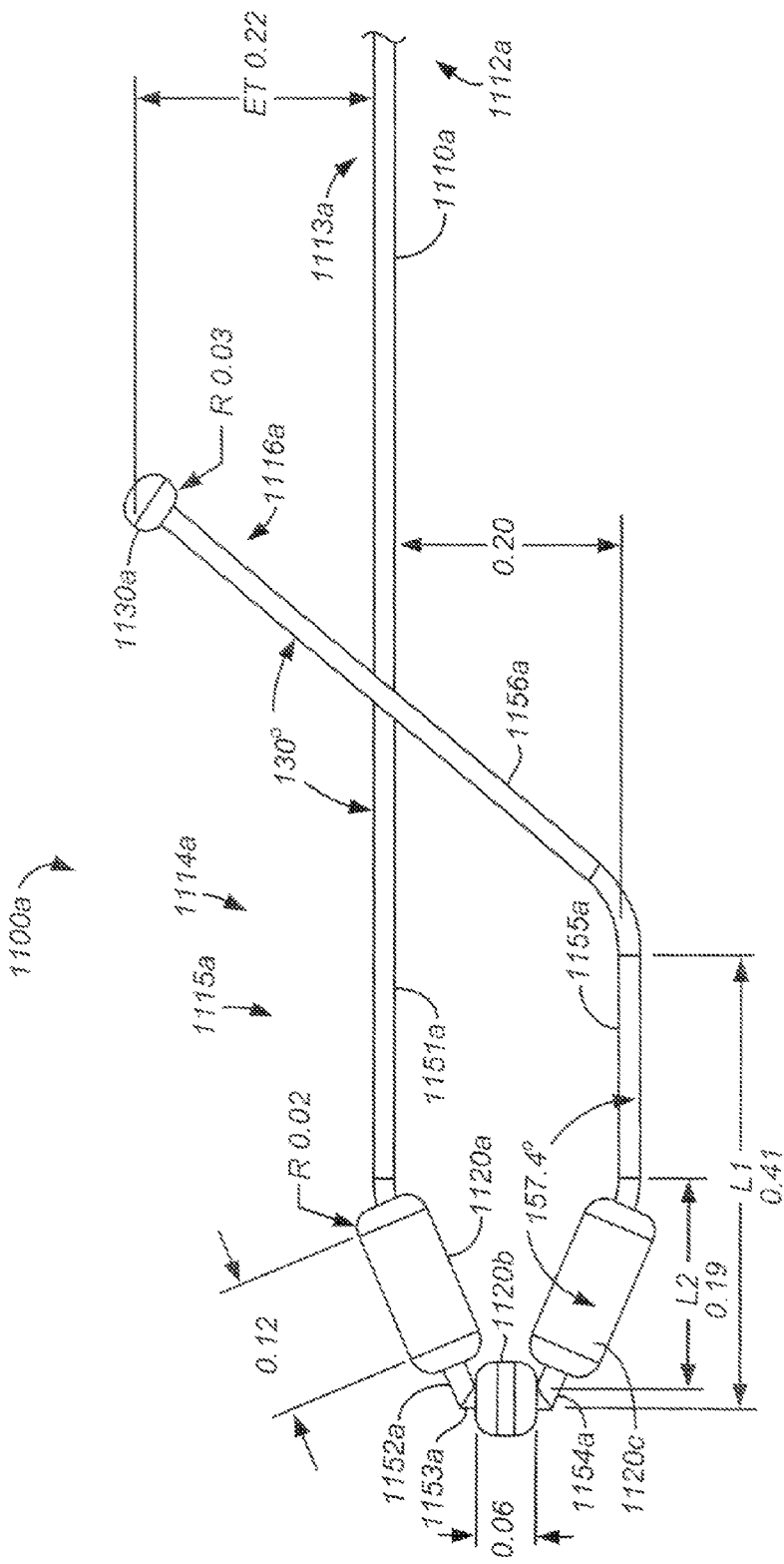

FIG. 11A illustrates side view of a snaring system 1100a according to embodiments of the present invention. As shown here, snaring system 1100a includes an elongate element or wire 1100a having a proximal portion 1112a and a distal portion 1114a. System 1100a can include a pin vice or handle (not shown) coupled with proximal portion 1114a of elongate element 1100a. As shown here, distal portion 1114a of elongate element 1100a includes a looped or hooked portion 1115a. Distal portion 1114a can also include a tag end 1116a. According to some embodiments, elongate element 1100a includes a stainless steel wire having a diameter of about 0.020 inches. Looped portion 1115a can have a first length L1 of about 0.41 inches and a second length L2 of about 0.19 inches. As shown here, tag end 1116a extends from a central portion 1113a of elongate element 1100a to a distance ET of about 0.22 inches. Snaring system 1100a includes three bearings or sleeves 1120a, 1120b, 1120c disposed about an elongate element 1100a. Snaring system 1100a also includes a distal bead or spherical mechanism 1130a disposed on a distal portion of elongate element 1110a.

Bearing 1120a presents a cylindrical or barrel shape having a diameter within a range from about 0.04 inches to about 0.10 inches. Optionally, bearing 1120a can have a diameter of about 0.07 inches. In some cases, bearing 1120a can have a length of about 0.12 inches. As shown here, an end portion of bearing 1120a presents a radius of curvature of about 0.2 inches. Bearing 1120b presents a spherical or oblate shape having a diameter within a range from about 0.04 inches to about 0.10 inches. Optionally, bearing 1120b can have a diameter of about 0.07 inches. In some cases, bearing 1120b can have a length of about 0.06 inches. Bearing 1120c presents a cylindrical or barrel shape having a diameter within a range from about 0.04 inches to about 0.10 inches. Optionally, bearing 1120c can have a diameter of about 0.07 inches. In some cases, bearing 1120c can have a length of about 0.19 inches. As shown in FIG. 11A, elongate element 1100a can have an angled bottom or distal looped portion, such that a first section 1151a is angularly offset from a second section 1152a. In turn, second section 1152a is angularly offset from a third section 1153a, which is angularly offset from a fourth section 1154a. Further, fourth section 1154a is angularly offset from a fifth section 1155a, which is angularly offset from a sixth section 1156a. As shown here, fourth section 1154a and fifth section 1155a of elongate element 1110a define an angle of about 157.4 degrees, and fifth section 1155a and sixth section 1156a of elongate element 1110a define an angle of about 130 degrees. Distal bead or spherical mechanism 1130a can present a radius of curvature of about 0.03 inches. Typically, the bottom or distal looped portions of the elongate element, optionally in combination with the bearings, are appropriately sized or configured to accommodate a pacing lead.

Figure 11B:
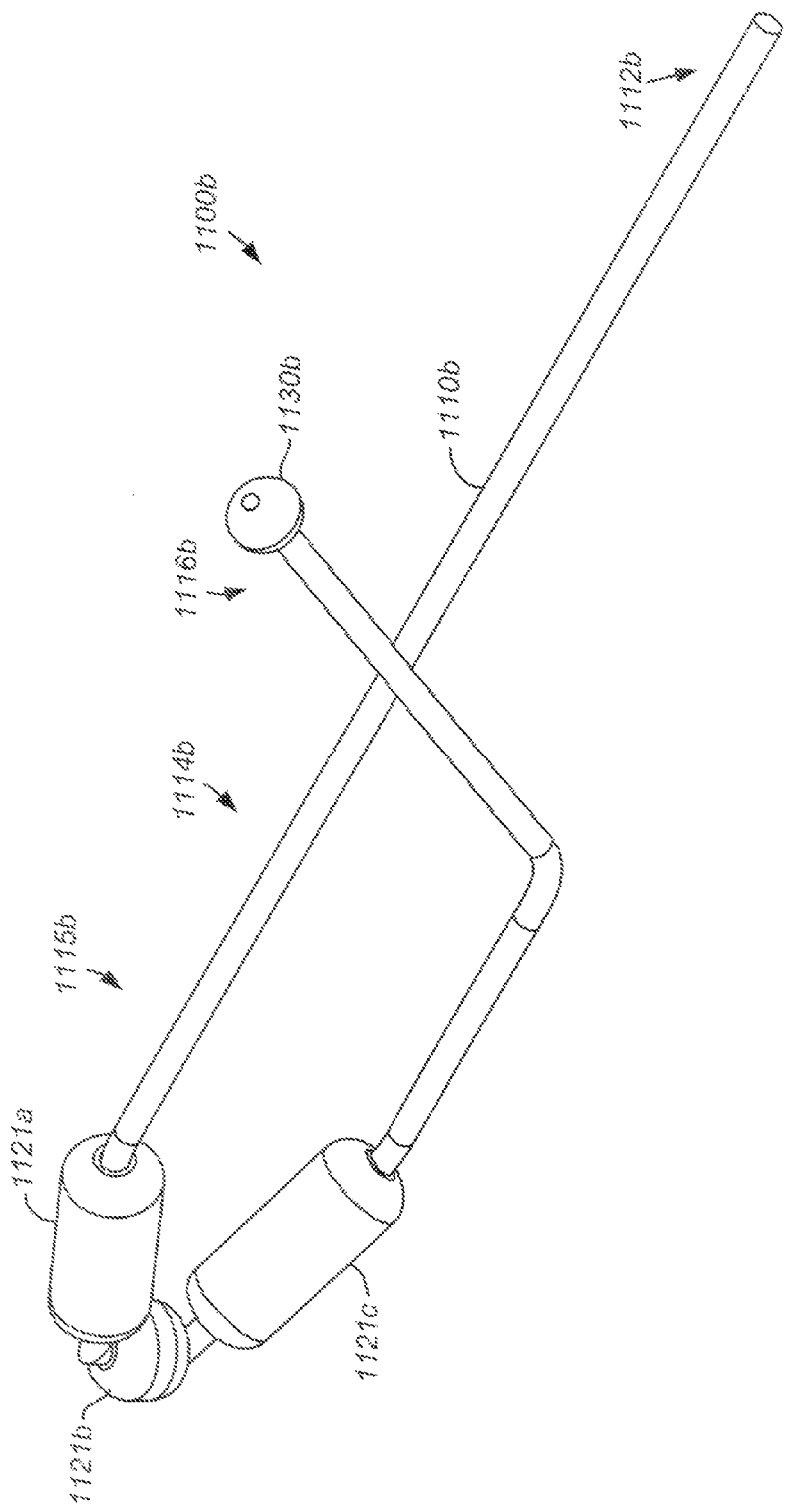

FIG. 11B illustrates a perspective view of a snaring system 1100b according to embodiments of the present invention. As shown here, snaring system 1100b includes an elongate element or wire 1110b having a proximal portion 1112b and a distal portion 1114b. System 1100b can include a pin vice or handle (not shown) coupled with proximal portion 1114b of elongate element 1110b. As shown here, distal portion 1114b of elongate element 1110b includes a looped or hooked portion 1115b. Distal portion 1114b can also include a tag end 1116b. According to some embodiments, elongate element 1110b includes a stainless steel wire having a diameter of about 0.020 inches. Elongate element 1110b and looped portion 1115b can present geometrical configurations similar to those described above with reference to FIG. 11A. Snaring system 1100b includes three bearings or sleeves 1121a, 1121b, 1121c disposed about an elongate element 1110b. Snaring system 1110b also includes a distal bead or spherical mechanism 1130b disposed on a distal portion of elongate element 1110b. The bearings and bead mechanisms can present geometrical configurations similar to those described above with reference to FIG. 11A.

Figure 11C:
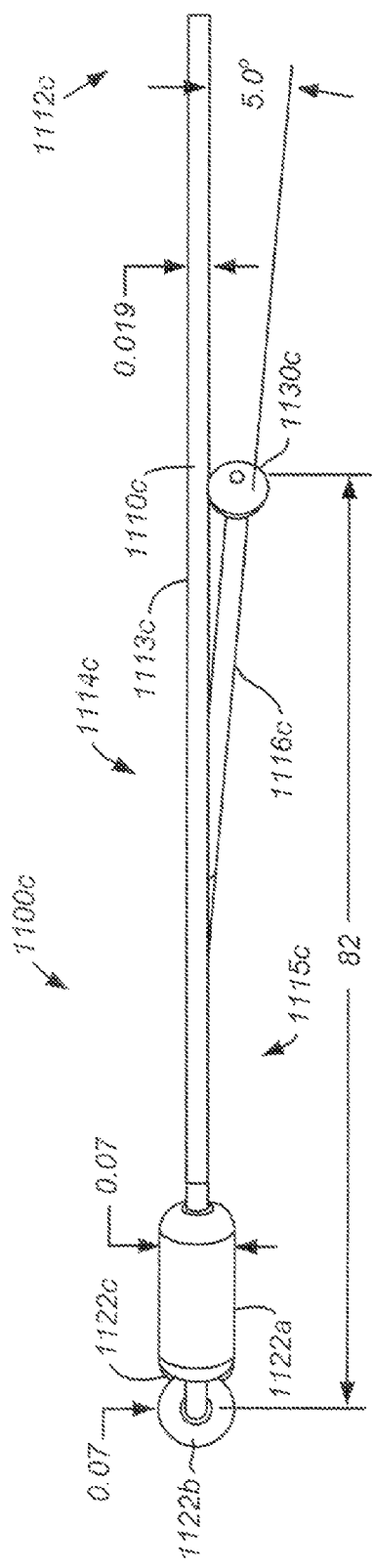

FIG. 11C illustrates a top view of a snaring system 1100c according to embodiments of the present invention. As shown here, snaring system 1100c includes an elongate element or wire 1110c having a proximal portion 1112c and a distal portion 1114c. System 1100c can include a pin vice or handle (not shown) coupled with proximal portion 1114c of elongate element 1110c. As shown here, distal portion 1114c of elongate element 1110c includes a looped or hooked portion 1115c. Distal portion 1114c can also include a tag end 1116c. According to some embodiments, elongate element 1110c includes a stainless steel wire having a diameter of about 0.019 inches. Elongate element 1110c and looped portion 1115c can present geometrical configurations similar to those described above with reference to FIG. 11A. Snaring system 1100c includes three bearings or sleeves 1122a, 1122b, 1122c disposed about an elongate element 1110c. Snaring system 1100c also includes a distal bead or spherical mechanism 1130c disposed on a distal portion of elongate element 1110c. The bearings and bead mechanisms can present geometrical configurations similar to those described above with reference to FIG. 11A. As shown here, tag end 1116c can be offset from a central portion 1113c of elongate element 1110c at an angle of about 5 degrees.

According to some embodiments, a hook can be radiopaque, for example by either being constructed of a base material having a suitable thickness, or by incorporating radiopaque material. In some cases, a hook or elongate element can contain radiopaque marker bands placed at appropriate or desired locations along the element. In some cases, a hook or coil can include a radiopaque metal such as Pt, Au, Ir, Tungsten, or the like. As noted, snaring systems can also include a hook or elongate element in conjunction with one or more bearing surfaces. A bearing or sleeve can include a low friction material such as Teflon, PE, nylon, or the like, optionally in a tubular or sheath configuration. The bearing or sleeve can be disposed or placed over the wire or elongate element. Optionally, a bearing or sleeve can be placed or positioned over a hard metal or plastic component mounted on the wire or elongate element, and can be designed or configured to rotate when a pacing lead is pulled out of the body with the snare system.

Figure 12A:
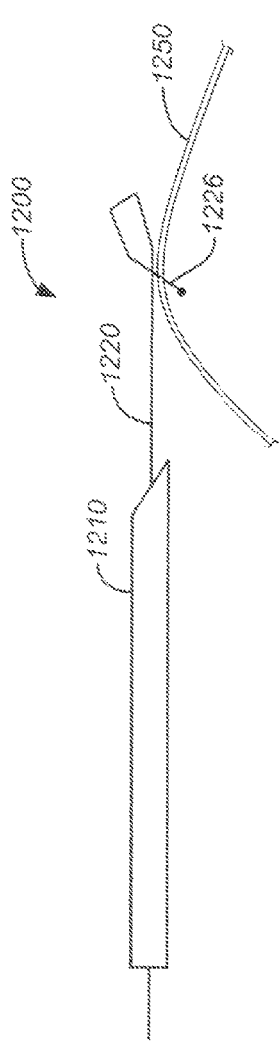
FIGS. 12A to 12C depict aspects of a snaring system according to embodiments of the present invention.
Figure 12B:
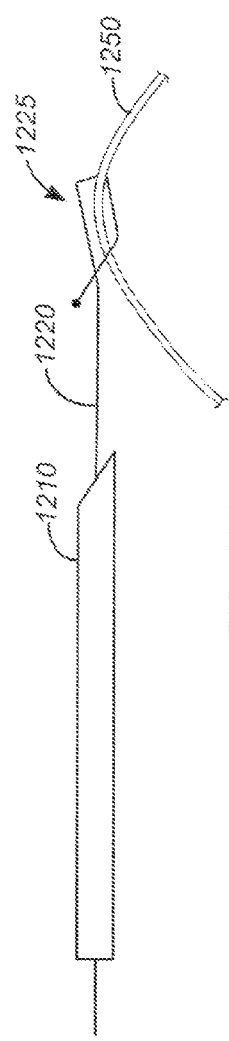
Figure 12C:
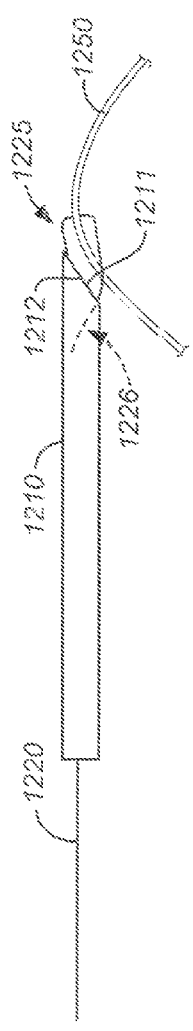

According to some embodiments, a snare system can include an outer jacket, such as a plastic sheath. FIG. 12A illustrates aspects of a snaring system 1200 according to embodiments of the present invention. Snaring system 1200 includes an outer jacket or sheath 1210 and a capture mechanism or elongate element 1220. An operator can position the snaring system so as to capture a portion of a pacing lead 1250 with a hook tag end 1226 of the elongate element. As shown in FIG. 12B, an operator can maneuver the snaring system, for example by pulling and rotating the elongate element, so as to enclose pacing lead 1250 within a distal loop 1225 of the elongate element. As shown in FIG. 12C, an operator can maneuver the snaring system, for example by advancing or translating sheath 1210 relative to elongate element 1220, so as to bring distal loop 1225 toward sheath 1210, such that hook tag end 1226 is received within the sheath, and pacing lead 1250 is securely grasped by distal loop 1225. In some instances, distal loop 1225 operates to squeeze or press the pacing lead against a distal end 1212 of sheath 1210.

Snaring systems which include a hook tag end as described herein are well suited for loosely engaging and maneuvering a pacing lead without subjecting the pacing lead to significant pulling forces. Such systems are particularly useful in pacing lead removal methods such as those described herein with reference to FIGS. 7A and 7B. For example, in some cases, it may be desirable or beneficial for the physician to administer a pulling action, wherein the pacing lead is not firmly grasped by the snaring system, but instead is more loosely engaged by the snaring system, such that he snaring system allows movement of the pacing lead through a snaring loop of the system as the system is navigated or manipulated by the physician.

According to some embodiments, outer jacket or sheath 1210 of the snaring system can have an inner or central lumen. In some cases, sheath 1210 can have an inner diameter of about 0.18 inches and an outer diameter of about 0.22 inches. Sheath 1210 can have a bevel 1211 disposed at distal end 1212. In some cases, sheath 1210 can present a 12Fr sheath. In some cases, sheath 1210 can be embodied by an outer sheath which is used in conjunction with a laser sheath.

FIG. 13A shows an outer sheath 1300 of a snaring system according to embodiments of the present invention. As shown here, sheath 1300 has a length L of about 32 cm to about 33 cm. Sheath 1300 includes an angled distal end 1310 that presents an angle a of about 40 degrees to about 45 degrees. Both distal end 1310 and proximal end 1320 are beveled or chamfered, to reduce or remove burrs or frays that may be present. As depicted in FIG. 13B, sheath 1300 can have an inner diameter ID of about 0.176 inches, and an outer diameter OD of about 0.2205 inches.

Experimental Results

Selected systems and methods were tested for performing pacing lead extraction via a jugular access site. For a jugular approach, it is possible to snare the implanted pacing lead and pull a proximal portion of the pacing lead up through the right jugular vein. A pacing lead is typically long enough to extend out the neck, and allow placement of a locking stylet. A jugular approach presents a straight anatomic approach to binding sites in the superior vena cava and ventricle areas. It is possible to free the pacing lead in the subclavian and innominant vein with a sheath, which can also be used as part of a snaring method to remove the pacing lead via the jugular vein.

A glass venous heart model was fitted with Tygon tubing of approximately 1" diameter, to exceed the model to the jugular and femoral entry sites. Small and medium simulated leads were placed in the model in the superior configuration and secured on the distal end by hemostats at the ventricular apex.

In an initial trial, a pigtail catheter that was tested with the heart model. The pigtail catheter was inserted though the jugular access site, in an attempt to grab the pacing lead from above. This trial was not successful, because the pigtail curve was not strong enough to pull the pacing lead up and through.

FIG. 14A illustrates a snaring system 1400 that was also tested with the heart model. Snaring system 1400 includes an elongate element 1410 having a distal end 1420 and a proximal end 1430. System 1400 also includes a pin device 1440 coupled with proximal end 1430 of the elongate element. Distal end 1420 includes a loop 1422 and a tag 1424. The elongate element 1410 includes a stainless steel wire having a 0.020 inch diameter. As depicted herein, distal section 1420 includes a straight bend 1421 which allows engagement of tag end 1424 with a pacing lead, for example, when rotating the hook or loop 1422 via rotation of pin vice 1440. Once tag 1424 is engaged with the pacing lead, a slight pull applied to the snaring system can secure the pacing lead in loop 1422. The first attempt using this design was successful in pulling the pacing lead up and out the jugular.

As depicted in FIG. 14B, snaring system 1400 may also include an outer sheath 1450. In use, sheath 1450 can be employed to secure loop 1422, for example by receiving the tag within a central lumen or distal opening 1452 of the sheath. In this way, snaring system 1400 can further cinch or grasp a pacing lead 1460. The tag end may remain covered by sheath 1450 while the snaring system is used to remove or maneuver the pacing lead.

FIG. 15 shows aspects of a snaring system 1500 which provided excellent results when used in the heart model. The snaring system includes an elongate element 1510 having a distal end 1520 and a proximal end 1530. Distal end 1520 includes a loop 1522 and a tag 1524. Snaring system 1500 also includes a sleeve or bearing 1560 disposed toward distal end 1520 of elongate element 1510. For example, bearing 1560 can be disposed about a portion of loop 1522. It was discovered that by using this system, the pacing lead could be maneuvered up and out the jugular vein of the in vitro model, using reduced pulling forces. Moreover, the elongate element can conveniently fit within a 12Fr. outer sheath, and can be used to effectively remove or maneuver a 12Fr. pacing lead. As shown here, bearing 1560 is disposed toward a distal end, or bottom, of loop or hook 1522.

FIG. 15A illustrates a side view of a snaring system 1500a according to embodiments of the present invention. The snaring system includes an elongate element 1510a having a distal portion 1520a and a proximal portion 1530a. Distal portion 1520a includes a loop 1522a and a tag 1524a. Snaring system 1500a also includes a sleeve or bearing 1560a disposed toward distal portion 1520a of elongate element 1510a. For example, bearing 1560a can be disposed about a portion of loop 1522a. Bearing 1560a can have a length of about 0.13 inches, and may present a radius of curvature of about 0.2 inches. As shown here, bearing 1560a is disposed toward a distal end, or bottom, of loop or hook 1522a. Distal portion 1520a can also include a tag end 1524a. According to some embodiments, elongate element 1510a includes a stainless steel wire having a diameter of about 0.020 inches. In some cases, tag end 1524a can extend from a central portion 1513a of elongate element 1510a to a distance of about 0.24 inches. Tag end 1524a can include a distal curve or bend 1525a.

As depicted in FIG. 15A, elongate element 1510a can have an angled bottom or distal looped portion, such that a first section 1551a is angularly offset and separated from a third section 1553a by a second section 1552a. In turn, third section 1553a is angularly offset and separated from a fifth section 1555a by a fourth section 1554a. Further, fifth section 1555a is angularly offset and separated from a seventh section 1557a by a sixth section 1556a. Second section 1552a can present a radius of curvature of about 0.07 inches, and fifth section 1555a can have a length of about 0.34 inches. Relatedly, first section 1551a can be disposed parallel to fifth section 1555a, such that first section 1551a and fifth section 1555a are separated by a distance of about 0.18 inches. First section 1551a and seventh section 1557a can be angularly offset, so as to define an angle of about 129.6 degrees. As shown here, rotatable bearing 1560a can be disposed on a section 1553a of loop 1522a, and loop 1522a can include a section 1555a distal to the section 1553a, and a section 1551a proximal to the section 1553a. Sections 1551a and 1555a can be in substantial parallel alignment. Relatedly, section 1553a can be in substantial perpendicular alignment with each of the sections 1551a and 1555a.

Figure 15B:
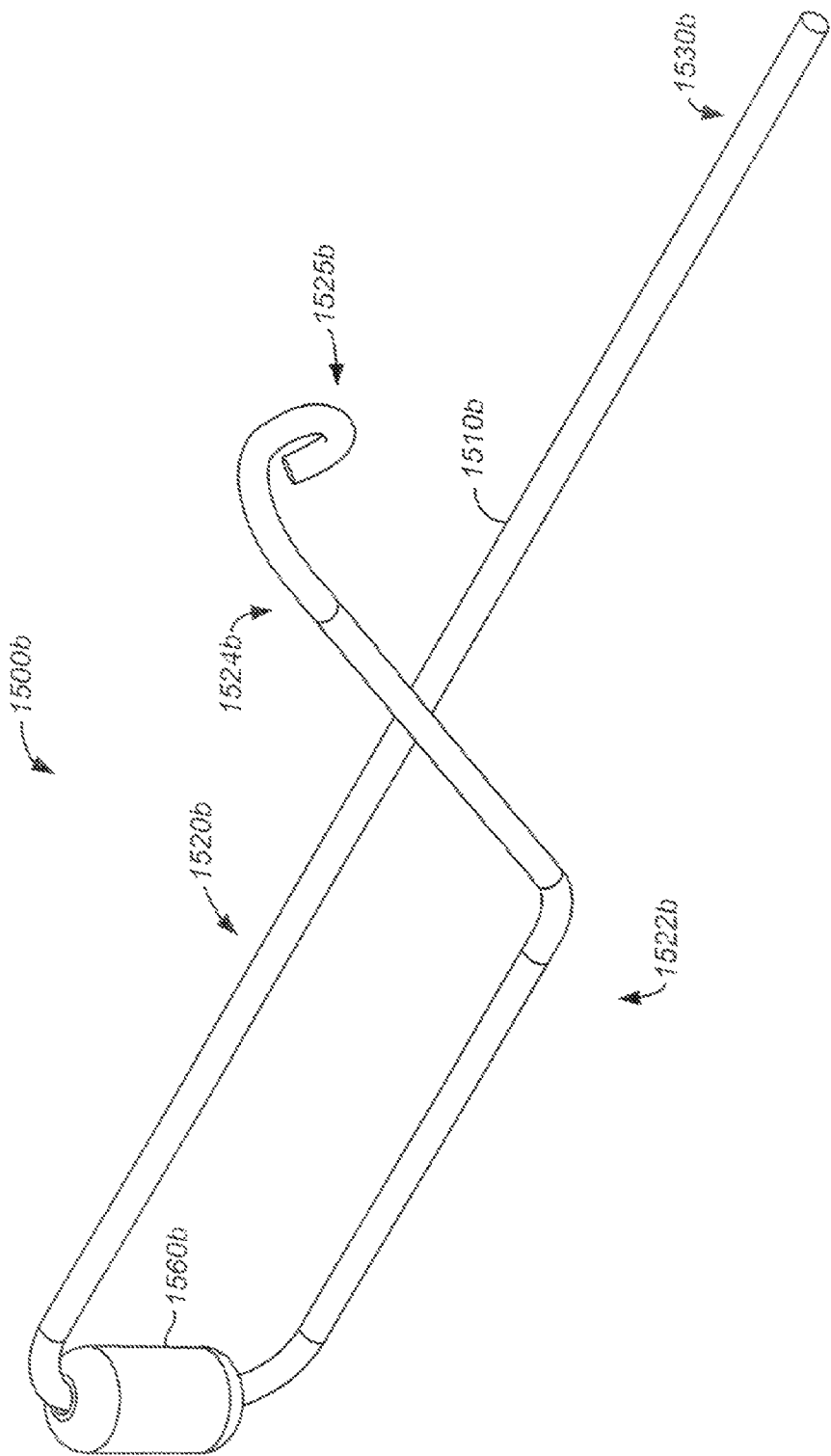
FIGS. 15 to 15C depict aspects of a snaring system according to embodiments of the present invention.

FIG. 15B illustrates a perspective view of a snaring system 1500b according to embodiments of the present invention. As shown here, snaring system 1500b includes an elongate element or wire 1510b having a proximal portion 1530b and a distal portion 1520b. System 1500b can include a pin vice or handle (not shown) coupled with proximal portion 1530b of elongate element 1510b. As shown here, distal portion 1520b of elongate element 1510b includes a looped or hooked portion 1522b. Distal portion 1520b can also include a tag end 1524b. According to some embodiments, elongate element 1510b includes a stainless steel wire having a diameter of about 0.020 inches. Elongate element 1510b and looped portion 1522b can present geometrical configurations similar to those described above with reference to FIG. 15A. Snaring system 1500b includes a bearing or sleeve 1560b disposed about elongate element 1510b. Snaring system 1500b also includes a distal curve or bend mechanism 1525b disposed on a distal portion of elongate element 1510b. The bearings and bend mechanisms can present geometrical configurations similar to those described above with reference to FIG. 15A.

Figure 15C:
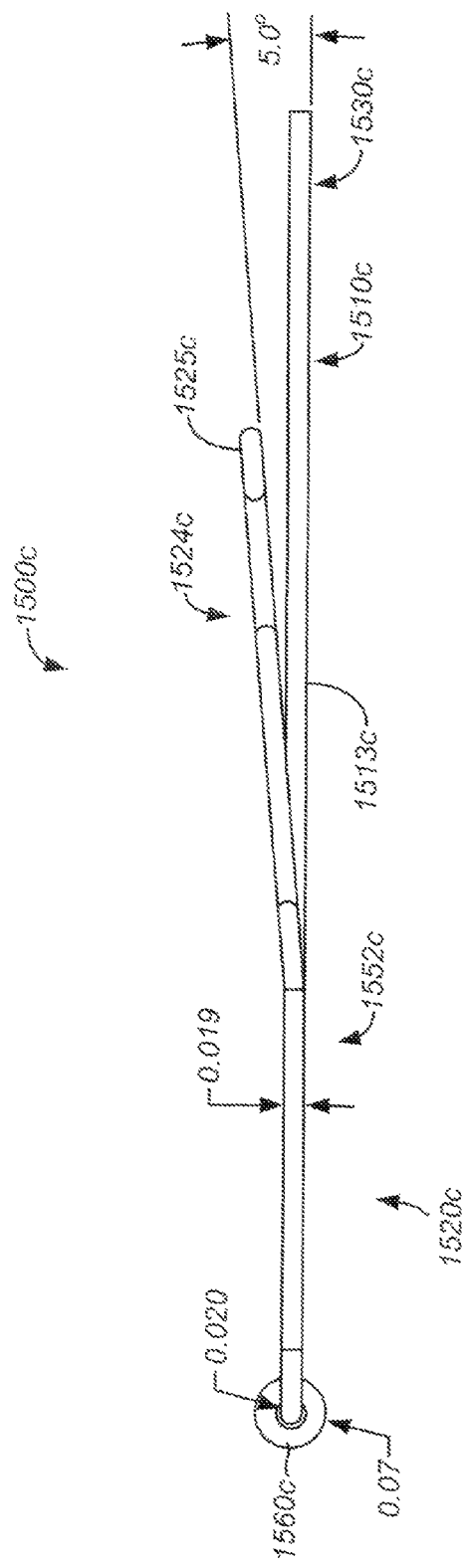

FIG. 15C illustrates a bottom view of a snaring system 1500c according to embodiments of the present invention. As shown here, snaring system 1500c includes an elongate element or wire 1510c having a proximal portion 1530c and a distal portion 1520c. System 1500c can include a pin vice or handle (not shown) coupled with proximal portion 1530c of elongate element 1510c. As shown here, distal portion 1520c of elongate element 1510c includes a looped or hooked portion 1522c. Distal portion 1520c can also include a tag end 1524c. According to some embodiments, elongate element 1510c includes a stainless steel wire having a diameter of about 0.019 inches. Elongate element 1510c and looped portion 1552c can present geometrical configurations similar to those described above with reference to FIG. 15A. Snaring system 1500c includes a bearing or sleeve 1560c. In some cases, bearing 1560 has an inner diameter of about 0.02 inches, and an outer diameter of about 0.07 inches. Snaring system 1500c also includes a distal bend or curve mechanism 1525c disposed on a distal portion of elongate element 1510c. The bearing and bend mechanisms can present geometrical configurations similar to those described above with reference to FIG. 15A. As shown here, tag end 1524c can be offset from a central portion 1513c of elongate element 1510c at an angle of about 5 degrees.

Hence, snaring systems according to embodiments of the present invention are well suited for use in grasping or maneuvering pacing leads. Such systems can be conveniently used in conjunction with a locking stylet which provides reliable unlocking. Systems may also be used in conjunction with or incorporate introducers placed at an access site. For example, a snaring system can be used with an introducer at a jugular entry site. In some cases, an introducer may include a valve. Snaring systems may be reversible, and thus can be used to easily grasp and release a pacing lead. Moreover, snaring systems may include a tag end or other atraumatic feature which provides protection at or near a distal portion of the system, and thus prevents or reduces the likelihood of damaging a patient tissue.

According to some embodiments, a snare can be inserted into the jugular vein of a patient. The snare can be used to grasp the pacing lead and push it down into the right atrium. Once the pacing lead is positioned as desired in the right atrium, the snare may be slid down the pacing lead so that it may grasp the pacing lead near the free end. Once grasped near its free end, the pacing lead may be pulled out through the jugular vein. In some cases, grasping snare wires can be extended or advanced through a wall of a catheter body.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A snaring system for engaging an object within a patient's body, the system comprising:
  a sheath having a sidewall, a central longitudinal axis and a lumen laterally offset from the central longitudinal axis;
  an elongate element extending through at least a portion of the lumen, wherein the elongate element has a proximal end and a distal end, the distal end comprising a loop;

a first rotatable bearing disposed along the loop at the distal end of the elongate element, the first rotatable bearing having a first length;

a second rotatable bearing disposed along the loop at the distal end of the elongate element, the second rotatable bearing having a second length, the second length being less than the first length; and a third rotatable bearing disposed along the loop at the distal end of the elongate element, wherein the second rotatable bearing is disposed along the loop at the distal end of the elongate element between the first rotatable bearing and the third rotatable bearing, the third rotatable bearing having a third length, and the third length being greater than the second length.

2. The snaring system of claim 1, wherein the loop terminates at a tag end, the tag end being disposed proximally relative to the first rotatable bearing, the second rotatable bearing, and the third rotatable bearing.

3. The snaring system of claim 2, wherein the lumen of the sheath is configured to receive the tag end.

4. The snaring system of claim 1, wherein the loop comprises a single wire.

5. The snaring system of claim 1, wherein the elongate element comprises a member selected from the group consisting of a flattened portion, a square cross-section portion, and a rectangular cross-section portion.

6. The snaring system of claim 1, further comprising a deflection mechanism coupled with the sheath and configured to deflect the sheath and the elongate element.

7. The snaring system of claim 1, wherein the first rotatable bearing and the third rotatable bearing each have a tubular shape.

8. The snaring system of claim 7, wherein the second rotatable bearing has a spherical shape.

9. The snaring system of claim 1, wherein the second rotatable bearing has a spherical shape.

10. The snaring system of claim 1, wherein the first rotatable bearing defines a first central longitudinal axis and the second rotatable bearing defines a second central longitudinal axis, and wherein the first central longitudinal axis is angularly offset from the second central longitudinal axis.

11. The snaring system of claim 10, wherein the third rotatable bearing defines a third central longitudinal axis, and wherein the third central longitudinal axis is angularly offset from the second central longitudinal axis.

12. A method of engaging an object disposed within a patient, the method comprising:

inserting a snaring system through an access site of a patient, wherein the snaring system comprises:

an elongate element having a proximal end and a distal end, the distal end comprising a loop;

a sheath having a sidewall, a central longitudinal axis and a lumen in the sidewall and laterally offset from the central longitudinal axis through which the elongate element extends;

a first rotatable bearing disposed along the loop at the distal end of the elongate element, the first rotatable bearing having a first length;

a second rotatable bearing disposed along the loop at the distal end of the elongate element, the second rotatable bearing having a second length, the second length being less than the first length;

a third rotatable bearing disposed along the loop at the distal end of the elongate element, wherein the second rotatable bearing is disposed along the loop at the distal end of the elongate element between the first rotatable bearing and the third rotatable bearing, the third rotatable bearing having a third length, and the third length being greater than the second length;

engaging the object with at least one of the first rotatable bearing, the second rotatable bearing, and the third rotatable bearing; and withdrawing the snaring system toward the access site, so as to move at least a portion of the object toward the access site.

13. The method of claim 12, wherein engaging the object further comprises sliding the elongate element within the lumen.

14. The method of claim 12, wherein the loop terminates at a tag end, the tag end being disposed proximally relative to the first rotatable bearing, the second rotatable bearing, and the third rotatable bearing, and wherein engaging the object further comprises moving the tag end into the lumen.

15. The method of claim 12, wherein the first rotatable bearing and the third rotatable bearing each have a tubular shape.

16. The method of claim 15, wherein the second rotatable bearing has a spherical shape.

17. The method of claim 12, wherein the second rotatable bearing has a spherical shape.

18. The method of claim 12, wherein the first rotatable bearing defines a first central longitudinal axis and the second rotatable bearing defines a second central longitudinal axis, and wherein the first central longitudinal axis is angularly offset from the second central longitudinal axis.

19. The method of claim 18, wherein the third rotatable bearing defines a third central longitudinal axis, and wherein the third central longitudinal axis is angularly offset from the second central longitudinal axis.

20. The method of claim 12, wherein the loop comprises a single wire.

* * * * *